(12) United States Patent
Kawaragi

(10) Patent No.: US 7,783,102 B2
(45) Date of Patent: Aug. 24, 2010

(54) DEFECT DETECTING APPARATUS, DEFECT DETECTING METHOD, INFORMATION PROCESSING APPARATUS, INFORMATION PROCESSING METHOD, AND PROGRAM THEREFOR

(75) Inventor: Hiroshi Kawaragi, Hokkaido (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 12/516,605

(22) PCT Filed: Nov. 30, 2007

(86) PCT No.: PCT/JP2007/001336

§ 371 (c)(1),
(2), (4) Date: May 28, 2009

(87) PCT Pub. No.: WO2008/068895

PCT Pub. Date: Jun. 12, 2008

(65) Prior Publication Data

US 2010/0074516 A1 Mar. 25, 2010

(30) Foreign Application Priority Data

Dec. 4, 2006 (JP) .............................. 2006-327102

(51) Int. Cl.
*G06K 9/00* (2006.01)
(52) U.S. Cl. .................................................. 382/145
(58) Field of Classification Search .................. 382/145
See application file for complete search history.

(56) References Cited

U.S. PATENT DOCUMENTS

| 5,563,702 A | 10/1996 | Emery et al. |
| 5,572,598 A | 11/1996 | Wihl et al. |
| 5,737,072 A | 4/1998 | Emery et al. |
| 6,052,478 A | 4/2000 | Wihl et al. |
| 6,363,166 B1 | 3/2002 | Wihl et al. |
| 6,535,621 B1 * | 3/2003 | Fujita .......................... 382/112 |

(Continued)

FOREIGN PATENT DOCUMENTS

JP          05-182887 A          7/1993

(Continued)

OTHER PUBLICATIONS

International Search Report for PCT/JP2007/001336 dated Jan. 8, 2008.

*Primary Examiner*—Bhavesh M Mehta
*Assistant Examiner*—Hadi Akhavannik
(74) *Attorney, Agent, or Firm*—Pearne & Gordon LLP

(57) ABSTRACT

A defect detecting apparatus captures an image of a protein chip formed on each die of a wafer with a low magnification for every first division region obtained by dividing each die in plurality; stores each obtained image as an inspection target image together with an ID for identifying each first division region; creates a model image for every first division region by calculating an average luminance value of pixels of each inspection target image; extracts a difference between the model image and each inspection target image as a difference image; determines presence of a defect by extracting a Blob having an area larger than a preset value from the difference image; captures a high-magnification image of every second division region; creates a model image again and extracts a Blob; and determines the kind of the defect based on a feature point of the defect.

17 Claims, 15 Drawing Sheets

U.S. PATENT DOCUMENTS

| | | |
|---|---|---|
| 6,584,218 B2 | 6/2003 | Wihl et al. |
| 7,068,363 B2 | 6/2006 | Bevis et al. |
| 7,424,146 B2 * | 9/2008 | Honda et al. ............... 382/149 |
| 2003/0063792 A1 * | 4/2003 | Hiroi et al. ............... 382/149 |
| 2004/0246476 A1 | 12/2004 | Bevis et al. |
| 2005/0117796 A1 * | 6/2005 | Matsui et al. ............. 382/145 |

FOREIGN PATENT DOCUMENTS

| | | |
|---|---|---|
| JP | 06-213820 A | 8/1994 |
| JP | 06-308040 A | 11/1994 |
| JP | 11-073513 A | 3/1999 |
| JP | 2001-091228 A | 4/2001 |
| JP | 2001-185591 A | 7/2001 |
| JP | 2002-323458 A | 11/2002 |
| JP | 2003-308803 A | 10/2003 |
| JP | 2004-077390 A | 3/2004 |
| JP | 2004-093317 A | 3/2004 |
| JP | 2004-150895 A | 5/2004 |
| JP | 2004-317190 A | 11/2004 |
| JP | 2005-156475 A | 6/2005 |
| JP | 2005-265661 A | 9/2005 |
| JP | 2006-100707 A | 4/2006 |
| JP | 2006-242900 A | 9/2006 |

* cited by examiner (a)

(b)

DEFECT DETECTING APPARATUS, DEFECT DETECTING METHOD, INFORMATION PROCESSING APPARATUS, INFORMATION PROCESSING METHOD, AND PROGRAM THEREFOR

TECHNICAL FIELD

The present invention relates to a defect detecting apparatus capable of detecting a defect such as a foreign substance, a flaw, and the like by performing a visual inspection of a microstructure such as MEMS (Micro Electro Mechanical Systems) formed on a semiconductor wafer, and also relates to a defect detecting method, an information processing apparatus, an information processing method, and a program to be used therefor.

BACKGROUND ART

Recently, MEMS devices, which integrate various functions in mechanical, electronic, optical and chemical field by using a micro-fabrication technology or the like, are attracting attention. As examples of MEMS device that have been in practical use so far, there are various sensors such as an acceleration sensor, a pressure sensor, an air flow sensor, and the like, which are used in an automobile or a medical field. In particular, MEMS devices are applied to a print head used in an inkjet printer, a micro mirror array used in a reflective type projector, or other various actuators. Besides, MEMS devices are also used as, for example, a protein analysis chip (so-called a protein chip), a DNA analysis chip, or the like in the field of chemical synthesis, bio-analysis, or the like.

Meanwhile, since the MEMS devices are very fine microstructures, it is important to detect defects such as foreign substances, flaws or the like present on the external appearances of the MEMS devices in a manufacturing process thereof. Conventionally, a visual inspection of the MEMS devices has been manually carried out by using a microscope. However, such inspection takes a lot of time and may cause a determination error because the inspection is carried out with naked eyes of an inspector.

Here, as an example of a technology for automating the visual inspection, disclosed in Patent Document 1 is a method for determining whether an inspection target object is normal or abnormal by capturing images of a plurality of normal products among inspection target objects by using, e.g., a CCD (Charge Coupled Device) camera or the like; storing them in a memory as a plurality of normal product images; calculating an average and a standard deviation of luminance values of pixels at the same position on the respective normal product images after performing position alignment of each normal product image; and then comparing the calculated average and standard deviation of the luminance value with a luminance value of each pixel on an image of an inspection target object.

Further, disclosed in Patent Document 2 is a method for detecting a pattern defect in a pattern inspection of a circuit board, a printed object or the like, wherein the method involves the steps of: creating reference image data to be used as a standard of normal products by way of capturing images of a plurality of reference patterns, storing the respective reference pattern images, aligning the position of each respective reference pattern, performing a calculation for obtaining an average value or a median value between the respective image data for every pixel, and creating the reference image data capable of being used as a proper standard by excluding highly deviated data or abnormal values; and then comparing the reference image data with inspection target image data.

Patent Document 1: Japanese Patent Laid-open Publication No. 2005-265661 (for example, FIG. 1)

Patent Document 2: Japanese Patent Laid-open Publication No. H11-73513 (for example, paragraph [0080])

Patent Document 3: Japanese Patent Laid-open Publication No. 2001-185591 (for example, paragraphs [0050]~[0053])

DISCLOSURE OF THE INVENTION

Problems to Be Solved by the Invention

However, in the technologies disclosed in any one of Patent Documents 1 and 2, the normal product image data or the reference image data used as the inspection criteria (hereinafter, they are referred to as model image data) are created based on the images captured by photographing a plurality of normal products which is prepared separately from the inspection target images. Accordingly, prior to the creation of the model image data, a process for determining and selecting a normal product is required to be performed, and since this process needs to be performed manually, it takes much time and effort. Further, in the inspection of the microstructures such as the MEMS devices in which a very minute flaw or foreign substance is regarded as a defect, preparing an absolutely normal product (model) is difficult in the aspect of maintenance or management of model image data.

Moreover, in the technologies disclosed in Patent Documents 1 and 2, the images of the inspection target objects such as the circuit boards or the like are captured while they are mounted on a table individually. Thus, in case that there are individual variations, resulted from a manufacturing process, in the respective inspection target objects, there is a likelihood that such individual variations would be wrongly detected as defects, though they are not actual defects but individual variations resulted from a manufacturing process. As a result, inspection accuracy would be deteriorated.

Furthermore, depending on resolution when capturing the images of the inspection target objects, a minute defect may not be detected from the images, resulting in a failure of detecting the defect, or the size of the defect may not be recognized accurately. In this regard, disclosed in Patent Document 3 is a method for detecting presence or absence of a defect by first capturing a low-magnification image of an inspection target object, and then capturing a high-magnification image of its portion from which a defect is detected among the inspection target object, thus succeeding in detecting a minute defect that could not be found with a low magnification and recognizing the accurate size of the defect.

In the technology described in Patent Document 3, however, it is impossible to recognize the kind of the defect although prevention of the detection failure of the defect and the accurate recognition of the defect size may be possible. Accordingly, even if a defect is detected, it is impossible to determine whether such defect is recoverable or not, or to find out the cause of the defect. Thus, a post-process after the defect detection cannot be performed smoothly.

In view of the foregoing, the present invention provides a defect detecting apparatus capable of detecting a defect of a MEMS device with high accuracy and efficiency without a use of an absolute model image and also capable of determining the kind of the defect accurately; and also provides a defect detecting method, an information processing apparatus, an information processing method and a program to be used therefor.

Means for Solving the Problems

In accordance with one aspect of the present invention, there is provided a defect detecting apparatus including: an imaging unit for capturing, with a first magnification, an image of a microstructure formed on each of a plurality of dies on a semiconductor wafer, with respect to every first division region obtained by dividing each die in plurality; a storage unit for storing therein the image of each first division region together with first identification information for identifying a position of each first division region within each die as a first inspection target image; a model image creating unit for creating an average image as a first model image for the every first identification information, the average image being obtained by averaging, among the first inspection target images, the first inspection target images of respective first division regions having the corresponding first identification information over the dies; a detecting unit for detecting presence or absence of a defect of the microstructure on each first division region within one of the dies by comparing the first model image with each first inspection target image corresponding to the first identification information of the first model image; a control unit for controlling the imaging unit such that the imaging unit captures, with a second magnification higher than the first magnification, an image of the microstructure on the first division region from which the defect is detected and microstructures on respective first division regions, within other dies, corresponding to the first identification information of the first division region from which the defect is detected, with respect to every second division region obtained by dividing each first division region in plurality; controlling the storage unit to store therein the image of each second division region together with second identification information for identifying a position of each second division region within each die as a second inspection target image; and controlling the model image creating unit to create an average image as a second model image for every second identification information, the second average image being obtained by averaging, among the second inspection target images, the second inspection target images of respective second division regions having the corresponding second identification information over the dies; and a defect classifying unit for determining the kind of the detected defect by comparing the second model image with each second inspection target image corresponding to the second identification information of the second model image.

Here, the microstructure refers to so-called MEMS (Micro Electro Mechanical Systems). The imaging unit is, for example, a camera provided with an imaging device such as a CCD (Charge Coupled Device), a CMOS (Complementary Metal Oxide Semiconductor) sensor, or the like. Further, the kinds of the defect include, for example, a foreign substance, a flaw, a crack, and the like.

With this configuration, it is possible to perform a high-accuracy visual inspection of the microstructure although it is difficult to obtain an absolutely normal product model (sample) for creating the model image based on the image of each division region in the target of the inspection.

Furthermore, by detecting the presence or absence of the defect based on the first inspection target image captured with the first magnification and by accurately determining the kind of the defect based on the second inspection target image captured with the second magnification higher than the first magnification, a post-process after the detection can be performed smoothly depending on the kind of the detected defect.

In the defect detecting apparatus, the storage unit may store therein feature point data indicating each feature point of plural kinds of defects, the detecting unit may include a first difference extracting unit for extracting a difference between the first model image and each first inspection target image as a first difference image, and the defect classifying unit may include a second difference extracting unit for extracting a difference between the second model image and each second inspection target image as a second difference image, a feature point extracting unit for extracting a feature point of a defect in the extracted difference images, and a classifying unit for determining the kind of the defect by comparing the extracted feature point with the feature point data.

Here, the feature point may be, for example, the area of the defect, the circumferential length thereof, a noncircularity, an aspect ratio or the like. By storing the feature point data indicating such feature points, accurate determination of the detected defect is achieved.

In this case, the storage unit may include a unit for updating the feature point data based on the feature point extracted by the feature point extracting unit.

In this way, by updating the feature point data repeatedly, the number and the kind of feature points can be increased and by learning feature points of defects every time the detection of the defect is repeated, the accuracy of the determination of the defect can be improved.

In the defect detecting apparatus, the control unit may include a unit for calculating the number of pixels that the defect in the first difference image detected by the first difference extracting unit occupies within the first difference image and performing an image pickup with the second magnification for every second division region if the number of pixels is smaller than a preset value, and the defect classifying unit may determine the kind of the defect based on the first difference image if the image pickup with the second magnification is not performed.

In this way, the necessity of the image pickup with the second magnification can be determined based on the number of pixels that the defect occupies on the first difference image. Thus, in the event that the number of pixels of the defect is great enough for the determination of the defect, processing time and load can be reduced by detecting the defect based on the first difference image without the second-magnification image pickup and a post process afterward. As a result, the determination of the defect can be carried out more efficiently.

In the defect detecting apparatus, the model image creating unit may include a unit for calculating an average luminance value of every pixel constituting each inspection target image having the corresponding the identification information.

In this way, by calculating the average luminance value for every pixel of each inspection target image, non-uniformity of the respective images can be effectively compensated, so that a high-quality model image can be created and detection accuracy can be improved.

In the defect detecting apparatus, the imaging unit may successively capture the images of the microstructures on respective division regions having the corresponding identification information over the dies.

In this way, by predetermining the division regions on the same position of the respective dies and capturing them successively, the model image of each division region can be created efficiently and inspection efficiency can be improved.

Further, after capturing the images of the microstructures in all the division regions on one die, the imaging unit may capture the images of the microstructures in respective division regions on another die adjacent to the one die.

In this way, by successively capturing the image of each division region on the same position of the respective dies, the model image of each division region can be created efficiently and inspection efficiency can be improved.

In the defect detecting apparatus, the microstructures may be screening test vessels including: a plurality of recesses each having a thin film shaped bottom surface and introducing therein a reagent and an antibody which cross-reacts with the reagent; and a plurality of holes provided in the bottom surface of each recess to discharge the reagent which does not react with the antibody.

Here, the vessel may be a protein chip. Accordingly, for example, a crack or flaw of the thin film (membrane) of the protein chip or a foreign substance adhered to the thin film can be detected with high accuracy.

In this case, prior to averaging of the first inspection target images corresponding to the first identification information of the first model image and the second inspection target images corresponding to the second identification information of the second model image respectively, the model image creating unit may align respective positions of the first and second inspection target images based on the shape of each recess of the vessel on the first and second inspection target images.

In this way, by using the shape of each recess of the vessel, an overlapped position of the respective first and second inspection target images can be accurately aligned, so that higher-quality first and second model images can be created. Further, specifically, the position alignment is carried out by varying the relative position of each image by way of moving each image along X and Y directions or rotating it along θ direction.

Further, in this case, prior to the extraction of the differences, the first and second difference extracting units may align positions of the first model image and each first inspection target image, and align positions of the second model image and each second inspection target image, based on the shape of each recess of the vessel on the first and second model images and the shape of each recess on each first inspection target image corresponding to the first identification information of the first model image and each second inspection target image corresponding to having the second identification information of the second model image.

In this way, by using the shape of each recess of the vessel, an overlapped position of the first and second inspection target images and the first and second model images can be accurately aligned, so that the defect can be detected with higher accuracy.

In the defect detecting apparatus, the microstructure may be an electron beam irradiation plate including a plate member having a plurality of window holes for irradiating electron beams and a thin film provided to cover each window hole.

With this configuration, for example, a crack or a flaw of the thin film (membrane) of the electron beam irradiation plate or a foreign substance adhered to the thin film can be detected with high accuracy.

In this case, prior to averaging of the first inspection target images corresponding to the first identification information of the first model image and the second inspection target images corresponding to the second identification information of the second model image, the model image creating unit may align respective positions of the first and second inspection target images based on the shape of each window hole of the electron beam irradiation plate on the first and second inspection target images.

In this way, by using the shape of each window hole of the electron beam irradiation plate, an overlapped position of the first and second inspection target images can be accurately aligned, so that higher-quality first and second model images can be obtained.

Further, in this case, prior to the extraction of the differences, the first and second difference extracting units may align positions of the first model image and each first inspection target image, and align positions of the second model image and each second inspection target image, based on the shape of each window hole of the electron beam irradiation plate on the first and second model images and the shape of each window hole on each first inspection target image corresponding to the first identification information of the first model image and each second inspection target image corresponding to the second identification information of the second model image.

In this way, by using the shape of each window hole of the electron beam irradiation plate, the same position of the inspection target image and the model image can be accurately aligned, so that the defect can be detected with higher accuracy.

In accordance with another aspect of the present invention, there is provided a defect detecting method including: capturing, with a first magnification, an image of a microstructure formed on each of a plurality of dies on a semiconductor wafer, with respect to every first division region obtained by dividing each die in plurality; storing the image of each first division region together with a first identification information for identifying a position of each first division region within each die as a first inspection target image; creating an average image as a first model image for the every first identification information, the average image being obtained by averaging, among the first inspection target images, the first inspection target images of respective first division regions having the corresponding first identification information over the dies; detecting presence or absence of a defect of the microstructure on each first division region within one of the dies by comparing the first model image with each first inspection target image corresponding to the first identification information of the first model image; capturing, with a second magnification higher than the first magnification, an image of the microstructure on the first division region from which the defect is detected and microstructures on respective first division regions, within other dies, corresponding to the first identification information of the first division region from which the defect is detected, with respect to every second division region obtained by dividing each first division region in plurality; storing the image of each second division region together with second identification information for identifying a position of each second division region within each die as a second inspection target image; creating an average image as a second model image for every second identification information, the second average image being obtained by averaging, among the second inspection target images, the second inspection target images of respective second division regions having the corresponding second identification information over the dies; and determining the kind of the detected defect by comparing the second model image with each second inspection target image corresponding to the second identification information of the second model image.

In accordance with still another aspect of the present invention, there is provided an information processing apparatus including: a storage unit for storing therein a captured image with a first magnification, of a microstructure formed on each of a plurality of dies on a semiconductor wafer, with respect to every first division region obtained by dividing each die in plurality together with first identification information for identifying a position of each first division region within each die as a first inspection target image; a model image creating unit for creating an average image as a first model image, the average image being obtained by averaging, among the first inspection target images, the first inspection target images of respective first division regions having the corresponding first identification information over the dies; a detecting unit for detecting presence or absence of a defect of the microstructure on each first division region within one of the dies by comparing the first model image with each first inspection target image corresponding to the first identification information of the first model image; a control unit for controlling the storage unit to store therein captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image, and controlling the model image creating unit to create an average image as second model image for every second identification information, the second average image being obtained by averaging, among the second inspection target images, the second inspection target images of respective second division regions having the corresponding second identification information over the dies; and a defect classifying unit for determining the kind of the detected defect by comparing the second model image with each second inspection target image corresponding to the second identification information of the second model image.

Here, the information processing apparatus may be, for example, a computer such as a PC (Personal Computer), and it may be of a so-called notebook type or desktop type.

In accordance with still another aspect of the present invention, there is provided an information processing method including: storing a captured image with a first magnification, of a microstructure formed on each of a plurality of dies on a semiconductor wafer, with respect to every first division region obtained by dividing each die in plurality together with first identification information for identifying a position of each first division region within each die as a first inspection target image; creating an average image as a first model image, the average image being obtained by averaging, among the first inspection target images, the first inspection target images of respective first division regions having the corresponding first identification information over the dies; detecting presence or absence of a defect of the microstructure on each first division region within one of the dies by comparing the first model image with each first inspection target image corresponding to the first identification information of the first model image; storing captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image; creating an average image as a second model image for every second identification information, the second average image being obtained by averaging, among the second inspection target images, the second inspection target images of respective second division regions having the corresponding second identification information over the dies; and determining the kind of the detected defect by comparing the second model image with each second inspection target image corresponding to the second identification information of the second model image.

In accordance with still another aspect of the present invention, there is provided a program for executing, in an information processing apparatus, the processes of: storing a captured image with a first magnification, of a microstructure formed on each of a plurality of dies on a semiconductor wafer, with respect to every first division region obtained by dividing each die in plurality together with first identification information for identifying a position of each first division region within each die as a first inspection target image; creating an average image as a first model image, the average image being obtained by averaging, among the first inspection target images, the first inspection target images of respective first division regions having the corresponding first identification information over the dies; detecting presence or absence of a defect of the microstructure on each first division region within one of the dies by comparing the first model image with each first inspection target image corresponding to the first identification information of the first model image; storing captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image; creating an average image as a second model image for every second identification information, the second average image being obtained by averaging, among the second inspection target images, the second inspection target images of respective second division regions having the corresponding second identification information over the dies; and determining the kind of the detected defect by comparing the second model image with each second inspection target image corresponding to the second identification information of the second model image.

EFFECT OF THE INVENTION

In accordance with the present invention as described above, highly accurate and efficient detection of a defect of a MEMS device can be implemented without having to use an absolute model image, and the kind of the defect can be determined accurately.

BEST MODE FOR CARRYING OUT THE INVENTION

Hereinafter, embodiments of the present invention will be described in detail with reference to the accompanying drawings.

FIG. 1 is a configuration view of a defect detecting apparatus in accordance with an embodiment of the present invention. As illustrated in FIG. 1, the defect detecting apparatus 100 includes a wafer table 2 for holding thereon, e.g., a silicon semiconductor wafer 1 (hereinafter, simply referred to as a wafer 1); an XYZ stage 3 for moving the wafer table 2 along X, Y and Z directions of the figure; a CCD camera 6 for capturing an image of the wafer 1 from above; a light source 7 for illuminating the wafer 1 while the CCD camera 6 captures the image; an image processing PC (Personal Computer) 10 for controlling the operation of each component and performing image processing to be described later.

The wafer 1 is transferred onto the wafer table 2 by a non-illustrated transfer arm or the like and is attracted to and fixed on the wafer table 2 by, for example, an adsorption unit such as a non-illustrated vacuum pump or the like. Further, it may be also possible not to attract the wafer 1 onto the wafer table 2 directly but to prepare a separate tray (not shown) capable of holding the wafer 1 thereon and to attract and hold the tray instead while the wafer 1 is kept on the tray. As will be described later, in case that holes are formed in the wafer 1, for example, it may be difficult to vacuum-attract the wafer 1 directly. In such case, the adsorption method using the tray would be effective. On the wafer 1, there is formed a protein chip as a MEMS device. The defect detecting apparatus 100 is an apparatus for detecting a defect such as a foreign substance or flaw on the protein chip which is an inspection target object. Detailed explanation of the protein chip will be provided later.

The CCD camera 6 is fixed at a predetermined position above the wafer 1, and it is provided with a lens, a shutter (not shown), or the like. Based on a trigger signal outputted from the image processing PC 10, the CCD camera 6 captures an image of the protein chip, which is formed at a predetermined portion of the wafer, under the light emitted from the light source 7 while enlarging the image by the provided lens, and sends the captured image to the image processing PC 10. Further, the XYZ stage 3 varies the relative distance between the CCD camera 6 and the wafer 1 by moving the wafer 1 in vertical direction (Z direction), whereby a focal position can be varied when the CCD camera 6 takes the image of the wafer 1. Further, it may be also possible to vary the focal positions by means of moving the CCD camera 6 along the Z direction instead of moving the XYZ stage 3.

Further, the lens of the CCD camera 6 is made up of a zoom lens, and it can capture images of the protein chip in different magnifications by varying a focal distance. In the present embodiment, the magnification of the CCD camera is variable between two levels: about 7 times (low magnification) and about 18 times (high magnification). In case of the low magnification, the size of view is, e.g., about 680×510 ($\mu m^2$); and in case of the high magnification, the size of view is, e.g., about 270×200 ($\mu m^2$). However, the magnifications are not limited to these examples. Further, instead of the CCD camera 6, a camera provided with another type of imaging device such as a CMOS sensor can be used.

The light source 7 is fixed at a predetermined position above the wafer 1, and it includes, for example, a flash lamp made up of a high-luminance white LED or a Xenon lamp, a flash turn-on circuit for controlling the lightening of the flash lamp, and so forth. The light source 7 illuminates the predetermined portion of the wafer 1 by emitting light of high luminance during a preset period of time, e.g., for about several $\mu$ seconds, based on a flash signal outputted from the image processing PC 10.

The XYZ stage 3 includes a motor 4 for moving an X stage 11 and a Y stage 12 in X, Y and Z directions along a movement axis 13; and an encoder 5 for determining moving distances of the X and Y stages 11 and 12. The motor 4 may be, for example, an AC servo motor, a DC servo motor, a stepping motor, a linear motor, or the like, and the encoder may be, for instance, one of various kinds of motor encoders, a linear scale, or the like. Whenever the X stage 11 and the Y stage 12 are moved as much as a unit distance along the X, Y and Z directions, the encoder 5 generates an encoder signal as movement information (coordinate information) indicating the movements, and outputs the generated encoder signal to the image processing PC 10.

The image processing PC 10 receives the encoder signal inputted from the encoder 5, and outputs a flash signal to the light source 7 based on the received encoder signal, and also outputs a trigger signal to the CCD camera 6. Further, based on the encoder signal inputted from the encoder 5, the image processing PC 10 also outputs a motor control signal to the motor 4 to control the operation of the motor 4.

FIG. 2 sets forth a block diagram for illustrating the configuration of the image processing PC 10. As illustrated in FIG. 2, the image processing PC 10 includes a CPU (Central Processing Unit) 21, a ROM (Read Only Memory) 22, a RAM (Random Access Memory) 23, an input/output interface 24, a HDD (Hard Disk Drive) 25, a display unit 26 and a manipulation input unit 27, and the respective components are connected with each other via an internal bus 28.

The CPU 21 controls the whole operation of each component of the image processing PC 10 and performs various operations in the image processing to be described later. The ROM 22 is a non-volatile memory for storing therein programs required for driving the image processing PC 10, other various data or programs requiring no update, or the like. The RAM 23 is a volatile memory used as a working area of the CPU 21, and it functions to read out various data or programs from the HDD 25 or the ROM 22 and store them temporarily therein.

The input/output interface 24 is an interface for connecting the manipulation input unit 27, the motor 4, the encoder 5, the light source 7 and the CCD camera 6 with the internal bus 28 to perform an input of an operation input signal from the manipulation input unit 27 and an exchange of various signals with respect to the motor 4, the encoder 5, the light source 7 and the CCD camera 6.

The HDD 25 stores, in an embedded hard disk, an OS (Operation System), various programs for performing an image pickup process and an image processing to be described later, other various applications, image data such as the image of the protein chip as the inspection target image captured by the CCD camera 6 and a model image (to be described later) created from the inspection target image, various data to be used as reference in the image pickup process and the image processing, and so forth.

The display unit 26 includes, for example, a LCD (Liquid Crystal Display), a CRT (Cathode Ray Tube), or the like, and displays the image captured by the CCD camera 6 or various condition screens for the image processing. The manipulation input unit 27 includes, for example, a keyboard, a mouse, or the like, and inputs a manipulation from a user in the image processing or the like to be described later.

Now, the protein chip formed on the wafer 1 will be explained. FIG. 3 is a top view of the wafer 1. As illustrated in the figure, for example, 88 semiconductor chips 30 (hereinafter, simply referred to as chips 30 or dies 30) are formed on the wafer 1 in a grid pattern. Here, it should be noted that the number of the dies 30 is not limited to 88.

FIG. 4 is a top view showing one of the dies 30 of the wafer 1. As shown in FIG. 4, a protein chip 35 having a plurality of circular recesses 50 on its entire surface is formed on each die 30. Each die 30, i.e., each protein chip 35 has an approximately square shape, and the length s of one side thereof is within a range of, for example, about several millimeters (mm) to several tens of millimeters (mm). However, the dimension of the length is not limited to this example.

FIG. 5 shows enlarged views of one recess 50 of the protein chip 35. FIG. 5(a) is a top view of the recess 50, and FIG. 5(b) is a Z-directional cross sectional view of the recess 50.

As illustrated in FIG. 4 and FIG. 5, a thin film (membrane) 53 having a plurality of holes 55 is formed in a bottom surface 52 of each recess 50 of the protein chip 35. The holes 55 are formed over the entire circular bottom surface 52 of each recess 50. The diameter d1 of each recess 50 is, for example, hundreds of micrometers (μm), and the diameter d2 of each hole 55 is, for example, several micrometers (μm). Further, the depth (height from a top surface 51 to the bottom surface 52) h of the recess 50 is, for example, several hundreds of micrometers (μm). Here, it should be noted that these dimensions are not limited to the examples.

The protein chip 35 is a silicon vessel for mounting a carrier e.g., latex fine particles (latex beads) on the bottom surface 52 of the recess 50 and screening protein having a specific property of being adsorbed with the latex beads by antibody cross-reaction when an antibody (protein) is injected into the recess 50 as a reagent. The reagent (protein) which is not adsorbed with the latex beads is discharged out through the holes 55 on the bottom surface 52, so that only the protein having the specific property remains in the recess 50.

Here, a manufacturing method of the protein chip 35 will be explained simply. First, the thin film 53 such as a silicon oxide film or the like is formed on one side of the wafer 1 by a CVD (Chemical Vapor Deposition) method. Then, photoresist is coated on the other side of the wafer 1, and after removing unnecessary portions by a photolithography technique, etching is performed by using a resist pattern as a mask, whereby the plurality of recesses 50 are formed on the wafer 1 while the thin film 53 still remains. Then, photoresist is coated on the thin film 53 of each recess 50, and portions of the photoresist corresponding to the holes 55 are removed by the photolithography technique, and etching is performed by using a resist pattern as a mask. As a result, the protein chip 35 having the plurality of recesses 50 each having the thin film 53 provided with a plurality of holes 55, as illustrated in FIG. 5, can be obtained.

Hereinafter, an operation of the defect detecting apparatus 100 in accordance with the embodiment of the present invention, for detecting a defect of the protein chip 35 will be described. FIG. 6 provides a schematic flowchart to describe the operation of the defect detecting apparatus 100 until it detects a defect.

As described in FIG. 6, the CCD camera 6 first captures an image of each die 30, on which the protein chip 35 is formed, with the low magnification (step 101). To elaborate, each die is divided into, e.g., 18×13 (a total of 234) first division regions 71 as illustrated in FIG. 7, and an image of each division region 71 is obtained by the CCD camera 6 under the light of the light source 7. Here, the number and the aspect ratio of the first division regions 71 are not limited to the mentioned examples. Each of the first division regions 71 is previously assigned an ID for identifying its location, and the HDD 25 of the image processing PC 10 stores therein each ID. Based on these IDs, the image processing PC 10 can identify the first division regions 71 located at the same positions on different dies 30. Further, each die 30 is also assigned an ID, so that the image processing PC 10 can determine which one of the dies 30 each first division region 71 belongs to.

At this time, as described above, the image processing PC 10 outputs a motor driving signal to the motor 4 based on an encoder signal from the encoder 5, thereby moving the XYZ stage 3. Further, the image processing PC 10 also generates a trigger signal and a flash signal based on the encoder signal, and outputs the generated trigger signal and flash signal to the CCD camera 6 and the light source 7, respectively.

Each time the XYZ stage 3 is moved, the light source 7 emits light toward the protein chip 35 for every several micro (μ) seconds based on the flash signal, and under the light, the CCD camera 6 successively captures images of the respective first division regions 71 of the protein chip 35 on the wafer 1 at a speed of, e.g., about 50 sheets/second, based on the trigger signal.

FIG. 8 illustrates trajectories of image pickup positions when the CCD camera 6 captures the images of the respective first division regions 71 of the protein chip 35. In the present embodiment, two image pickup paths can be considered, as illustrated in FIG. 8.

As shown in FIG. 8(a), among the 88 dies 30 of the wafer 1, the CCD camera 6 starts to capture an image from, e.g., the leftmost die 30 among the dies 30 of which Y-coordinate values are maximum, and after successively capturing the images of all of the 18×13 first division regions 71 of the leftmost die 30, e.g., line by line, the CCD camera 6 proceeds to the next die 30 and captures images of all first division regions 71 thereon line by line again.

That is, the image processing PC 10 outputs the motor driving signal to the motor 4 such that the image pickup position for each first division region 71 of one die 30 starts from, e.g., the first division region 71 belonging to the uppermost line and the leftmost row and is then moved rightward along the X direction, and if it reaches the rightmost end, the image pickup position is moved along the Y direction by one line and then is moved leftward along the X direction, and also if it reaches the leftmost end, the image pickup position is moved by one line along the Y direction again and then is then moved rightward along the X direction on the next line. If the image pickup of all the first division regions 71 of one die 30 is completed by repeating the above-mentioned procedure, the image pickup position is moved to the adjacent next die 30, and the same movements are repeated. At this time, since the position of the CCD camera 6 is fixed, in fact, the XYZ stage 3 is moved along the opposite directions to those of the trajectory shown in FIG. 8(a). The CCD camera 6 successively captures the images of each first division region 71 based on the trigger signal outputted from the image processing PC 10 while keeping up with such movements.

Further, as illustrated in FIG. 8(b), the image pickup position can also be moved such that the CCD camera 6 successively captures the images of first division regions having the corresponding ID (located at the same positions) on the different dies 30.

That is, the image processing PC 10 sets the image pickup position of the CCD camera 6 to start from the leftmost die 30 among the dies 30 of which Y-coordinate values are maximum, for example, and drives the motor 4 such that the image pickup position of the CCD camera 6 is moved along X and Y directions to allow the CCD camera 6 to first pass through respective first division regions 71 (first division regions 71 marked by black circles) having the corresponding ID on the different dies 30 and having minimum X-coordinate values while having the maximum Y-coordinate values and then to pass through respective first division regions 71 (first division regions 71 marked by white circles) having the corresponding ID and located next to the first image pickup positions along the X direction, and then to repeat the movements of allowing the CCD camera 6 to pass through respective first division regions 71 located on the same positions on the different dies 30. Keeping up with such movements, the CCD camera 6 repeats the operation of successively capturing the images of the plurality of first division regions 71 having the corresponding ID for every die 30, based on the trigger signal outputted from the image processing PC 10.

The image processing PC 10 allows the CCD camera 6 to perform the image pickup operation by selecting one of the two image pickup paths which allows shorter image pickup time. In case that the image pickup path shown in FIG. 8(a) is selected, each image pickup interval between the first division regions 71, that is, the movement interval of the XYZ stage 3 is the same as each interval between the first division regions 71 whereas in case that the image pickup path shown in FIG. 8(b) is selected, the movement interval of the XYZ stage 3 is the same as each interval between the dies 30. Accordingly, the CPU 21 of the image processing PC 10 is capable of calculating a driving speed of the motor 4 based on these movement intervals and the image pickup frequency of the CCD camera 6. By multiplying the entire image pickup path shown in FIG. 8(a) or 8(b) determined by the layout of the dies 30 shown in FIG. 3 with this driving speed, the image pickup time that would be taken for capturing the images of the first division regions 71 of all the dies 30 can be estimated for each of the cases of FIG. 8. By comparing the image pickup times in both cases, the image processing PC 10 determines which one of image pickup paths shown in FIG. 8 will take shorter image pickup time, and selects the image pickup path that requires shorter image pickup time.

The images of the first division regions 71 captured by the CCD camera 6 are transmitted to the image processing PC 10 as inspection target images along with their IDs for identifying the first division regions 71, and are stored in the HDD 25 or the RAM 23 via the input/output interface 24 of the image processing PC 10. Further, in the present embodiment, though the size of the inspection target images captured by the CCD camera 6 is a so-called VGA (Video Graphics Array) size (640×480 pixels), the present invention is not limited to that size.

In the present embodiment, as the XYZ table 3 is moved along the Z direction, the distance between the protein chip 35 of the wafer 1 and the CCD camera 6 can be varied by the movement of the XYZ stage 3 as described above, thus enabling to capture images of the inspection target images at different focal positions. FIG. 9 provides the illustration of such operation.

As shown in FIG. 9, the XYZ stage 3 is moved in an upward direction (Z1 direction of FIG. 9) and in a downward direction (Z2 direction of FIG. 9) based on a focus signal from the image processing PC 10, thus varying the distance between the CCD camera 6 and the protein chip 35 in, for example, three levels (focal points F1 to F3). That is, as the XYZ stage 3 is moved along the Z2 direction, the CCD camera 6 focuses on the top surface 51 of the protein chip 35 (focal point F1), and as the XYZ stage 3 is further moved along the Z1 direction from there, the CCD camera 6 focuses on an approximately midway position between the top surface 51 and the bottom surface 52 of the protein chip 35 (focal point F2), and as the XYZ stage 3 is moved along the Z1 direction, the CCD camera 6 can focus on the bottom surface 52 of the protein chip 35 (focal point F3). Further, the number of the variable focal points is not limited to only three.

As described above, the defect detecting apparatus 100 in accordance with the present embodiment captures the inspection target images at the plurality of different focal points. Accordingly, even in case the inspect target object has a three-dimensional shape having thickness (depth or height) in the Z direction as in the case of the protein chip 35 in the present embodiment, it is possible to capture images at respective Z-directional positions and thus avoid failure to detect the defect. The CCD camera 6 classifies the images captured at each focal position through the path of FIG. 8(a) or 8(b) based on their focal positions, and then transmits them to the image processing PC 10. The image processing PC 10 identifies the images as the inspection target images for every focal position and then stores them in the HDD 25 or the RAM 28. That is, as described above, in case that the focal points are three, F1 to F3, the CCD camera 6 performs the image pickup process for every focal position by repeating three times of movements, along the image pickup path of FIG. 8(a) or 8(b).

Referring back to the flowchart of FIG. 6, while carrying out the above-described image pickup process by the CCD camera 6, the CPU 21 of the image processing PC 10 also performs a filtering process by means of a high pass filter for each acquired inspection target image every time the inspection target image is obtained from the CCD camera 6 (step 102).

The protein chip 35 in the present embodiment has the thin film 53 at the bottom surface 52 thereof. In the event that the thin film 53 is bent, for example, non-uniformity of luminance may be resulted due to a flatness of the thin film 53. Further, the non-uniformity of luminance may be caused due to, e.g., a deviation of an optical axis of the CCD camera 6 or a difference in degree of uniformity on the side where the light from the light source 7 reaches, or the like. Such luminance variability may be extracted as a difference in a difference extracting process to be described later, leading to erroneous defect detection.

A non-uniform luminance portion is a portion of the inspection target image where luminance is gradually varied. That is, the non-uniform luminance component can be referred to as a low frequency component. Here, in the present embodiment, this low frequency component is removed from each inspection target images by means of the high pass filter.

FIG. 10 presents a flowchart to describe the high pass filtering process in detail. As shown in FIG. 10, the CPU 21 of the image processing PC 10 reads out a duplicate of the inspection target image from the HDD 25 to the RAM 23 (step 61), and performs a Gaussian blurring process on the inspection target image (step 62). Further, though a set value for blurring is, for example, about 15 to 16 radius pixels, the present invention is not limited thereto.

In this Gaussian blurring process, since a pixel of a high frequency component (e.g., an edge portion) in the original inspection target image is blurred by a contribution from neighboring pixels of a low frequency component, a high blurring effect can be obtained. Meanwhile, as for the pixel of low frequency component (e.g., the non-uniform luminance portion) in the original inspection target image, neighboring pixels contributed thereto is also a low frequency component, so that the blurring effect is low, and a change from the original inspection target image can be hardly observed. Accordingly, an output image (hereinafter, referred to as a "Gaussian blur image") obtained by the Gaussian blurring process is an image having low frequency components left after high frequency components in the original inspection target image are smoothed.

Subsequently, the CPU 21 subtracts the Gaussian blur image from the original inspection target image (step 63). By subtracting, from the high frequency components of the original inspection target image, their corresponding low frequency components of the Gaussian blur image, only the original high frequency components are left. Further, by subtracting, from the low frequency components of the original inspection target image, their corresponding low frequency components of the Gaussian blur image, the original low frequency components are removed. That is, the image obtained by the subtraction process is an image having only the high frequency components left after removing the low frequency components from the original inspection target image. The CPU 21 updates the original inspection target image with the image acquired after the subtraction process and stores it in the HDD 25 (step 64).

Referring back to FIG. 6, the CPU 21 determines whether to perform an image pickup process of each inspection target image for every first division region 71 and whether to perform the filtering process with the high pass filter for every inspection target image (steps 103 and 104). If it is determined that the image pickup process of all the inspection target images and the filtering process therefor are performed (Yes), a process for creating a model image for each division region is performed by using the inspection target images after the filtering process (step 105). Further, in the present embodiment, though the image pickup process of the inspection target image and the high pass filtering process are performed in a parallel manner, it may be also possible to perform the high pass filtering process after completing the image pickup process of the inspection target for all of the first division regions 71 (that is, it may possible that a process of step 102 and step 103 are reversed in sequence).

Here, the process for creating the model image will be explained in detail. FIG. 11 provides a flowchart to describe a process sequence until the image processing PC 10 creates the model image, and FIG. 12 schematically illustrates the way in which the image processing PC 10 creates the model image.

As shown in FIG. 11, the CPU 21 of the image processing PC 10 reads out inspection target images, which have the corresponding ID over the dies 30 among the inspection target images after the high pass filtering process, from the HDD 25 to the RAM 23 (step 41), and performs position alignment of each read-out inspection target image (step 42). Specifically, among the inspection target images of the first division regions 71 present at the same position on the different dies 30, the CPU 21 recognizes, for example, the shapes of edge portions on the recesses 50 of the protein chips 35 and carries out the position alignment by controlling shifts in the X and Y directions and rotations in the θ direction to allow those shapes to be overlapped between the respective inspection target images.

For example, as illustrated in FIG. 12, the CPU 21 reads out inspection target images 40a to 40f, having the corresponding ID, captured for first division regions 71a present at the same position on the different dies 30. In the present embodiment, since the number of the dies 30 is 88, the total number of inspection target images 40 having the corresponding ID becomes 88, too. The CPU 21 overlaps all of the 88 inspection target images 40 together and aligns their positions based on the shapes of the recesses 50 or the like. As described, by performing the position alignment based on the shapes of the recesses 50 or the like, easy and exact position alignment can be realized.

Subsequently, in the state that the above-described position alignment is performable, the CPU 21 calculates an average pixel luminance value for every pixel on the same position among the respective inspection target images 40 (step 43). Upon the completion of the calculation of the average luminance values of all the pixels in each inspection target image 40 of the first division region 71a (Yes in step 44), based on the calculation result, the CPU 21 generates an image made up of pixels having these average luminance values as a model image 45, and stores it in the HDD 25 (step 45).

By repeating this process, the CPU 21 determines whether the model image 45 is created for each of the corresponding first division regions 71 between the dies 30 (step 46), and if it is determined that all the model images 45 are created (Yes), the process is finished.

By the above-described process, it is possible to create the model images 45 based on the actual inspection target images 40 even in the inspection of the MEMS devices for which acquisition of an absolute normal product sample is impossible. There is a likelihood that a defect such as a foreign substance, a flaw, a crack of thin film and the like may be present on each inspection target image 40. However, by dividing each die 30 into a multiplicity of (in the present embodiment, 234) first division regions 71 and calculating the average luminance values over the plurality of (in the present embodiment, 88) dies 30, the defect of each inspection target image 40 can be compensated, and it becomes possible to create the substantially ideal model images 45. Thus, highly accurate defect detection is enabled.

As described above, since each of the inspection target image 40 at a single first division region 71 is present for each of the focal points F1 to F3, the model image 45 is also created for each focal point. Accordingly, in the present embodiment, since the number of the first division regions 71 is 234 on each die 30, 234×3 (a total of 702) sheets of model images are created.

Referring back to the flowchart of FIG. 6, after the completion of creation of the model images 45, the CPU 21 performs a process for extracting a difference between the model images 45 and each inspection target image 40 after the high pass filtering process for every first division region 71 (step 106).

To elaborate, as in the case of the above-stated position alignment process for the creation of the model images 45, the CPU 21 performs position alignment along the X, Y, and θ directions based on the shapes of the recesses 50 present on the model images 45 and each inspection target image 40, and performs a binarization process by extracting the difference between the two images by a subtraction process and then outputs the result as a difference image.

Then, the CPU 21 performs filtering by a so-called Blob extraction for this difference image (step 107). Here, a Blob implies a cluster of pixels having a preset (or a preset range of) gray scale value on the difference image. From the difference image, the CPU 21 extracts only a Blob larger than a certain area (e.g., 3 pixels) among Blobs.

FIG. 13 shows difference images before and after the Blob extracting process. FIG. 13(a) illustrates a difference image 60 before the Blob extraction, and FIG. 13(b) illustrates a difference image after the Blob extraction (hereinafter referred to as a "Blob extraction image 65").

In FIG. 13(a), conspicuous white portions indicate differences between the model image 45 and the inspection target image 40. In this difference image 60, a process for enhancing luminance value as much as, e.g., about 40 times the luminance value of the original difference image is performed to emphasize the differences. As shown in FIG. 13(a), besides the defect such as the foreign substances, the flaws, and the like, the difference image 60 before the Blob extraction also has microscopic noises 84 observed as portions surrounded by white dashed lines due to various reasons such as contamination of the lens 14 of the CCD camera 6, the degree of uniformity of the illumination of the light source 7, and so forth. Since the presence of the noises 84 leads to wrong detection of defects, these noises 84 need to be eliminated.

The noises 84 have a smaller area than the area of defects such as foreign substances or flaws. Here, as illustrated in FIG. 13(b), the noises 84 can be eliminated by performing a filtering process for extracting only a Blob larger than a preset area by way of removing a Blob smaller than the preset area. By this Blob extracting process, only the cracks 81 of the thin film of the recess 50 of the protein chip 35 or foreign substances 82 such as dirt adhered to the protein chip 35 can be extracted from the Blob extraction image 65. At this time, the CPU 21 recognizes them just as defect candidates without determining the kinds of the defects such as the foreign substances, cracks, flaws, and the like.

Subsequently, referring back to the flowchart of FIG. 6, when a defect candidate is detected by the Blob extracting process (Yes in step 108), the CPU 21 determines whether it is necessary to capture a higher-magnification image of the protein chip 35 from which the defect candidate is detected (step 109). That is, the CPU 21 determines whether there has been inputted a user manipulation for instructing a pickup of a more detailed higher-magnification image of the first division region 71 to which the inspection target image 40 containing the defect candidate belongs. When it is determined that the pickup of higher-magnification image is necessary (Yes), the CCD camera 6 captures a high-magnification image of each of second division regions 72 in the first division region 71 from which the defect candidate is detected and the other first division regions 71 having the ID corresponding to that of this first division region 71 on the different dies 30, wherein the second division regions are obtained by dividing each first division region in a smaller unit (step 113).

In a defect classifying process to be described later, though determination of the defect and classification thereof are carried out based on the area of the extracted Blob, for example, it may be impossible to calculated the Blob area accurately in case that the Blob extraction image 65 is created based on the inspection target image captured with a low magnification. Further, with the low-magnification image, it can be deemed that an accurate shape of the defect may not be recognized and thus an exact classification of the defect may not be achieved. In the present embodiment, however, by capturing the higher-magnification image of the protein chip 35, determination of the defect and classification thereof, which will be described later, are enabled to be carried out accurately.

FIG. 14 schematically illustrates the high-magnification image pickup of each second division region 72 in the first division region 71 from which the defect candidate is detected. As can be seen from FIG. 14, in case that the defect candidate is detected from the inspection target image capturing a first division region 71a on a certain die 30, this first division region 71a is further divided into 3×3 (9 in total) second division regions 72. Further, on the other dies 30, the first division regions 71 having the ID corresponding to that of the first division region 71a are also further divided into second division regions 72. Like each first division region 71, each second division region 72 is assigned an ID for identifying its position on each die 30.

The CCD camera 6 captures an image of each second division region 72 in the same size (VGA size) as the first division region 71. That is, the CCD camera 6 captures the image of the second division region 72 by enlarging it three times as larger as that of the first division region 71. Each captured image is stored in, e.g., the HDD 25 of the image processing PC 10 as an inspection target image along with the ID of each second division region.

Moreover, as for an image pickup path for each second division region 72 of each die 30, a shorter path among those shown in FIG. 8 is selected, as in the case of the image pickup of the first division region 71. That is, the CPU 21 determines which path is shorter among a path through which the image pickup is first carried out for all the second division regions 72 of the first division region 71 of one die 30 and then carried out for each second division region 72 of the first division regions 71 corresponding to that of the different dies 30 and a path through which the image pickup is carried out in the sequence of the second division regions 72 having the corresponding ID among the corresponding first division regions 71 over the dies 30, and then performs the image pickup process through either shorter one of the two paths.

If the image pickup for the first division region 71 found to have the defect candidate and the second division regions 72 of the first division region corresponding thereto is completed (step 113), the CPU 21 performs a filtering process with the high pass filter (step 114) and a model image creating process (step 117) on each inspection target image, as in the processes of steps 102 to 107, and conducts a difference extracting process between a model image and each inspection target image captured on each second division region 72 of the first division region 71 from which the defect candidate is detected (step 118). The CPU then performs a filtering process by Blob extraction (step 119).

Further, since the inspection target image of each second division region 72 is captured with a higher resolution than that of the inspection target image of the first division region 71, a threshold value (pixel) of an Blob area extracted by the Blob extracting process in step 118 is set to be larger than a threshold value of the Blob area extracted by the Blob extracting process for each first division region 71 in step 107. However, it should be noted that there is no difference in the actual Blob area (μm), converted from the threshold value (pixel), on the protein chip 35.

FIG. 15 illustrates Blob extraction images 65 extracted from each inspection target image of the first division region 71 and the second division region 72. FIG. 15(a) shows a Blob extraction image 65a extracted from the first division region 71, and FIG. 15(b) shows a Blob extraction image 65b extracted from the second division region 72.

As can be seen from FIG. 15, in the Blob extraction image 65a of the first division region 71a obtained in step 107, a region viewed as a foreign substance 82 is conspicuously observed at a left lower end portion. However, since its area is small, it is difficult to calculate an exact value of area. Therefore, as shown in FIG. 15(b), by dividing the first division region 71 into 9 second division regions 72, and then capturing the high-magnification images of the second division regions 72 in which the foreign substance 82 is observed, that foreign substance 82 can be displayed with the high resolution, so that accurate calculation of its areas is enabled.

Further, in case that the defect candidate is extracted in step 108, it may be also possible to perform the high-magnification image pickup automatically without carrying out the process of determining the necessity for the high-magnification image pickup in step 109. Moreover, if the performance of the image processing PC 10, the motor 4 and the encoder 5 is excellent and the processing time is within an allowable range, it may be possible to create the model image 45 for all the second division regions 72 by capturing images of the second division regions 72 of all the first division regions 71 on every die 30 as well as the first division region 71 from which the defect candidate is extracted. In such case, it would be desirable to perform the image pickup process, the high pass filtering process and the model image creation process for every second division region 72 immediately after the completion of the Blob extracting process for the first division region 71 without determining the necessity of the high-magnification image pickup in step 109 and to perform the Blob extracting process for each second division region 72 of the first division region 71 which is determined to contain the detected defect candidate by the CPU 21.

Referring back to the flowchart of FIG. 6, when it is determined in step 109 that the high-magnification image pickup is not necessary (No) or when the Blob extracting process from the second division regions 72 in steps 113 to 119 is completed, the CPU 21 performs classification of the defect candidate shown in the Blob extraction image 65 (step 110).

That is, for each Blob marked white in the Blob extraction image 65, CPU 21 determines whether each Blob is a defect or not based on feature points such as its area, circumferential length, noncircularity, an aspect ratio and the like, and classifies the kind of the defect by determining whether the defect is a foreign substance, a flaw, a crack, or the like.

Specifically, the image processing PC 10 collects sample images of every kind of defects such as foreign substance, flaws, cracks and the like and stores feature point data in the HDD 25 or the like as a feature point database, and compares feature points detected from each Blob of the Blob extraction image 65 of the inspection target with the stored feature point data.

For example, one side of the foreign substance in the present embodiment ranges about several micrometers to tens of micrometers, and the length of the flaw range from about several micrometers to hundreds of micrometers. Further, when the foreign substance is compared with the flaw, the flaw has an aspect ratio with a very elongated width or length, and its circumferential length is also lengthened. Further, though a crack of the thin film is generated at the edge portion of the recess 50 in a curved shape, the noncircularity of the recess 50 is increased in comparison with a normal case. The image processing PC 10 stores these data as the feature point data, and carries out the classification of the defect by the comparison of the respective feature points of the detected Blob with the stored data.

Further, as described above, the protein chip 35 in the present embodiment has the holes of, e.g., several micrometers in the thin film 53 at the bottom surface of the recess 50, and the holes 55 serve to discharge the reagent. Accordingly, even when a foreign substance is adhered inside the recess 50, the foreign substance would be discharged through the holes 55 along with the reagent in case that the foreign substance has a diameter smaller than that of the holes 55 of several micrometers, thus causing no problem in screening using the protein chip 35. Thus, the diameter of the holes 55 will be set as a threshold value for the foreign substances, and a foreign substance having a smaller diameter than that will not be considered as a defect. Meanwhile, for a flaw or a crack, since the reagent leaks therefrom, normal screening cannot be performed. For the reason, the flaw or crack will be always considered as a defect.

As stated above, in the event that the feature points of the Blob extraction image 65 extracted from the first division region 71 cannot be measured accurately, the CPU 21 conducts the measurement of the feature points by using the Blob extraction image 65 obtained from the second division region 72 whose images are captured with the higher magnification, and performs classification of the various kinds of defects. As described above, by capturing the high-magnification images when necessary, a process after the defect detection can be performed effectively.

When the determination of the presence of defects and classification thereof are carried out for every defect candidate (Yes in step 111), Blob extraction images and information upon the kinds of the detected defects are outputted to, e.g., the display unit 26 as a detection result (step 112), and the process is finished. At this time, the image processing PC 10 may display, for example, an image allowing one-sight recognition of which kind of defect exists on which part of the wafer 1 on the display unit 26.

Based on the outputted result, when a foreign substance is found to exist, the user removes the foreign substance. Further, when a flaw or a crack is found to exist, that protein chip 35 is discarded as an abnormal product. Further, if no defect candidate is detected in step 108, the inspected protein chip 35 is determined as a normal product, and the defect detecting process is ended.

In accordance with the present embodiment, through the above-described operations, it becomes possible to create the model image based on the inspection target image of every first division region 71 or every second division region 72 even in case of the MEMS device such as the protein chip 35 for which obtaining an absolute normal sample is difficult. Therefore, high-accuracy defect detection is enabled. Further, since the model image 45 is created based on each inspection target image 40 captured under the same optical and illumination conditions, a wrong detection due to the difference in such conditions can be prevented.

The present invention is not limited to the above-described embodiment but can be modified in various ways without departing from the scope of the present invention.

In the above embodiment, though the protein chip is exampled as the MEMS device as the inspection target object, the MEMS device is not limited thereto. For example, an electron beam irradiation plate (EB window) can be applied as the MEMS device.

FIG. 16 illustrates the exterior view of the electron beam irradiation plate. FIG. 16(a) is a top view thereof, and FIG. 16(b) is a cross sectional view along a Z direction of FIG. 16(a).

As shown in FIG. 16, the electron beam irradiation plate 90 includes a plate 92 having a plurality of window holes 95 through which an electron beam EB is to be irradiated; and a thin film 91 configured to cover the window holes 95.

The plate 92 is formed in a rectangular shape having an X-directional length w and Y-directional length l of, e.g., several tens of millimeters and a Z-direction length h of, e.g., several millimeters. However, these lengths and shape are nothing more than examples, and the present invention is not limited thereto. Further, though each window hole 95 has a rectangular shape whose one side is, e.g., several millimeters, this length and shape is just examples, and the window hole can have a square shape instead. Moreover, though a total of 54 (6×9) window holes 95 are formed, the number of the holes is not limited thereto.

The electron beam irradiation plate 90 constitutes an electron beam irradiation apparatus by being connected with an end portion of a non-illustrated vacuum vessel. An electron beam EB irradiated from an electron beam generator installed inside the vacuum vessel is irradiated to the atmosphere through the window holes 95 and finally irradiated to a target object, as indicated by arrows in FIG. 16(b). The electron beam irradiation apparatus is used for various purposes including, e.g., sterilization and modification of physical property and chemical property of the target object to which the electron beam is irradiated. By forming the thin film 91, the electron beam can be irradiated while a vacuum state is maintained. Here, a multi-layered structure made up of a plurality of stacked thin films 91 can be used.

The electron beam irradiation plate 90 is formed on each die of the wafer 1 by an etching process using a photolithography technique or the like, like the protein chip 35 in the above-sated embodiment. In this case, each die has the same size as that of the plate 92.

The defect detecting apparatus 100 performs an image pickup process, a high pass filtering process, a model image creating process, a Blob extracting process and so forth for the electron beam irradiation plate 90, as in the case of the above-stated protein chip 35, and detects a defect such as a foreign substance, a flaw, a crack or the like present on the electron beam irradiation plate 90. Furthermore, image pickups are also possible with low-magnification and high-magnification and at plural focal points along the Z direction in the same manner. Moreover, in the model image creating process and the Blob extracting process, position alignment of each inspection target image is performed along the X, Y and θ directions such that edge shapes of the window holes 95 shown in each inspection target object are overlapped.

Moreover, in case of a inspection of the electron beam irradiation plate 90, as for feature points for the classification of defects such as a threshold value for determination of a foreign substance or the like, the image processing PC 10 creates independent feature point data based on samples and the like of the electron beam irradiation plate 90, unlike the case of the inspection of the protein chip 35, and classifies the defects based on the data.

In addition, besides the protein chip 35 and the electron beam irradiation plate 90, various other MEMS devices, e.g., sensors such as an acceleration sensor, a pressure sensor, an air flow sensor and the like, a print head of an inkjet printer, a micro mirror array of a reflective projector, other kinds of actuators, various types of bio chips and the like can also be applied as an inspection target object.

In the above described embodiment, though the images necessary for the image processing, such as the inspection target images 40, the model images 45, the difference images 60 and the Blob extraction images 65, are stored in the HDD 25, they can be temporarily stored in the RAM 23 instead or can be temporarily stored in a buffer region separate from the RAM 23 and deleted as soon as the defect classifying process is completed. Further, among the inspection target images, images from which no difference is extracted through the difference extraction, that is, images from which no defect is detected are not necessary in the following process. Thus, they may be deleted in sequence from a time point when no detection of defect is determined. Furthermore, when capturing the high-magnification images of the second division regions 72 for the inspection target images of the first division regions 71 captured with the low magnification, the inspection target images of the first division regions 71 become unnecessary after the image pickup of the second division regions 72, so that they may be deleted at a time point when the image pickup of the second division regions 72 is completed. In the above-described embodiment, since the number of the captured images is great, the amount of data stored in the RAM 23 or the HDD 25 can be reduced by processing as stated above, so that the load of the image processing PC can be reduced.

In the above-stated embodiment, though the necessity of the high-magnification image pickup is determined based on, for example, presence or absence of the user's manipulation input, it may be also possible to allow the image processing PC 10 to calculate the number of pixels of defect candidates present on the Blob extraction images extracted based on the inspection target images of the first division regions 71 and the model images and perform the high-magnification image pickup when the number of pixels exceeds a preset number.

That is, in case that a defect candidate is shown as a large pixel area enough to distinguish the kind of the defect among the Blob extraction images extracted from the inspection target images of the first division regions 71, classification of the defect is performed at that moment, whereas in case that the pixel area thereof is small and the area of the defect candidate cannot be calculated accurately or the shape of the defect candidate can not be recognized accurately, classification of the defect is performed in detail by the high-magnification image pickup of it. In this way, since the necessity of the high-magnification image pickup is determined based on the defect area and then classification of the defect is performed, more efficient classification of the defect is enabled.

In the above-described embodiment, it may be also possible to store the images of the defect candidates Blob-extracted based on the inspection target images of the first and second division regions and the model images in the feature point database of the HDD 25 additionally and update the feature point database whenever necessary. In this case, since the image processing PC studies the feature point data every time it repeats the defect detecting process, the accuracy of the defect classification can be improved gradually.

EXPLANATION OF CODES

Figure 1:
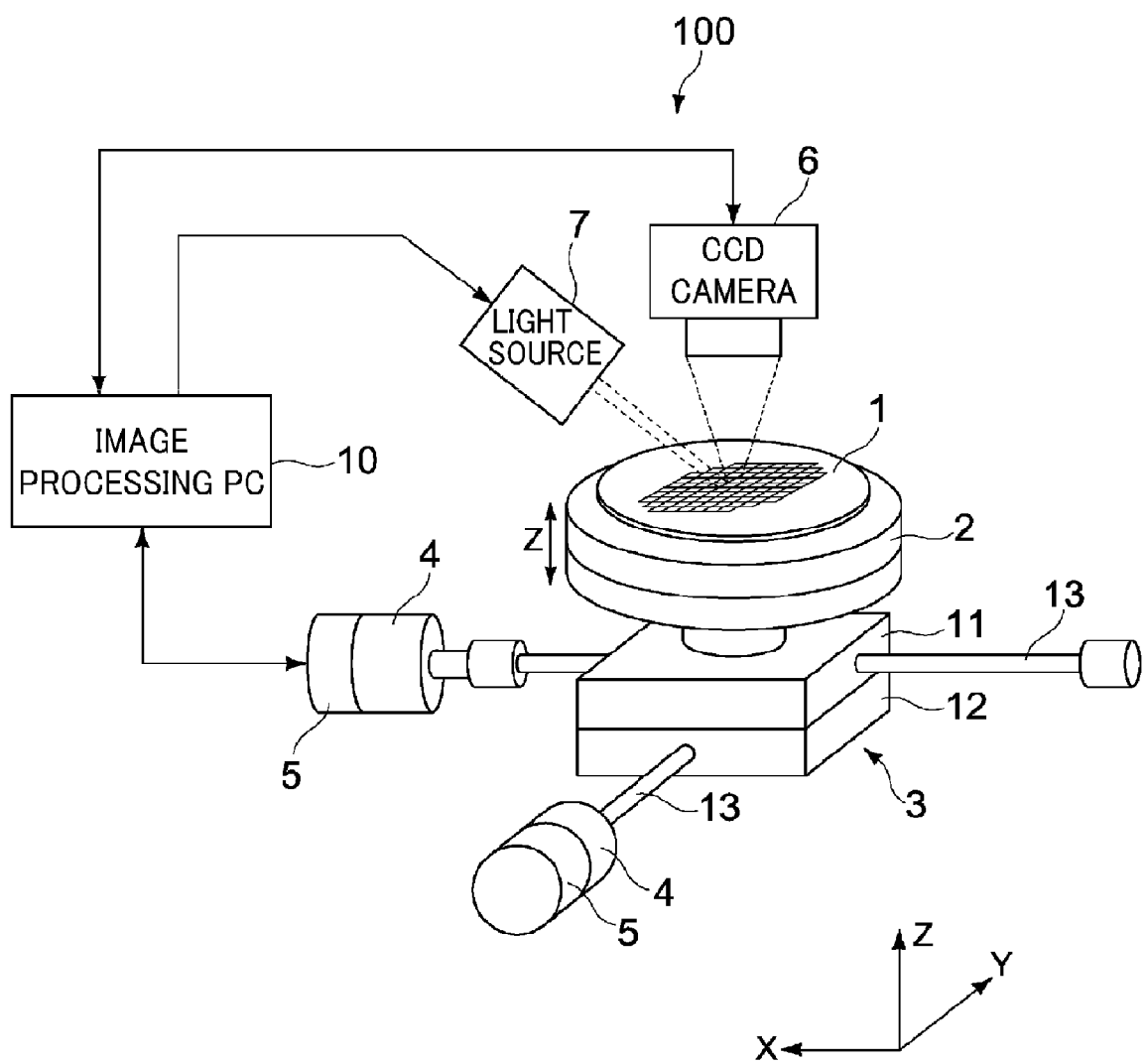
FIG. 1 provides a configuration view of a defect detecting apparatus in accordance with an embodiment of the present invention.
Figure 2:
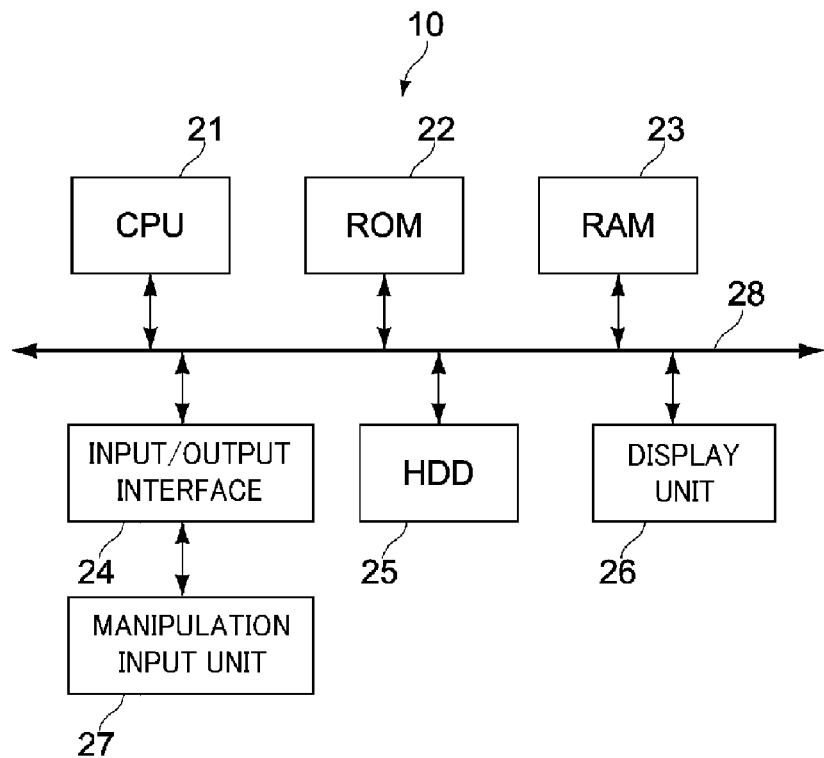
FIG. 2 sets forth a block diagram illustrating the configuration of an image processing PC in accordance with the embodiment of the present invention.
Figure 3:
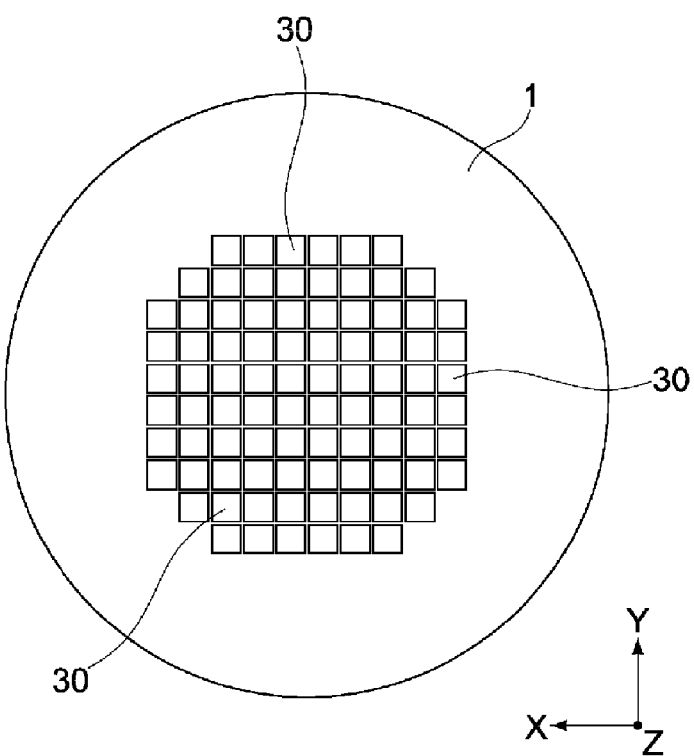
FIG. 3 depicts a top view of a wafer in accordance with the embodiment of the present invention.
Figure 4:
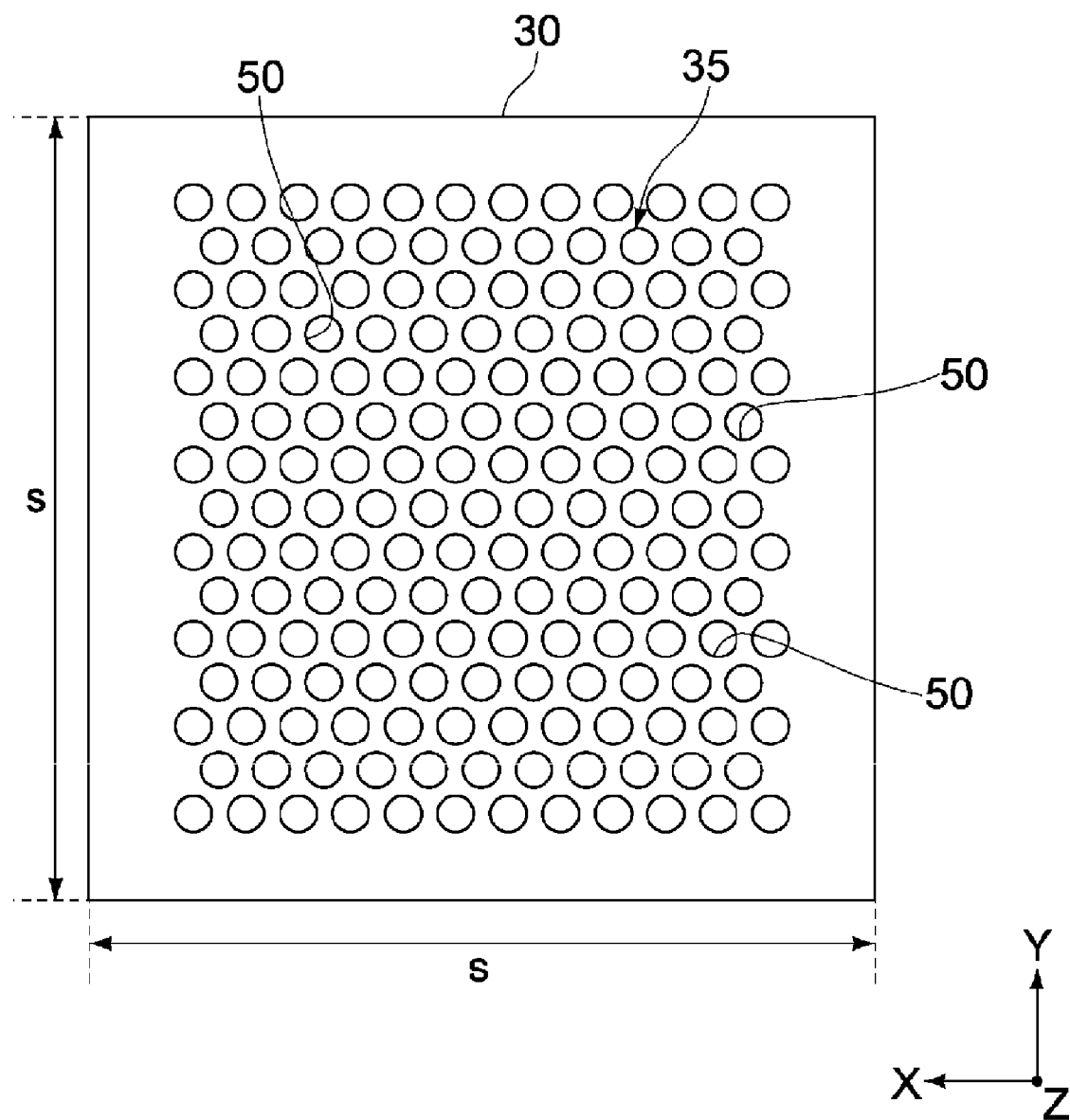
FIG. 4 presents a top view of one of dies of the wafer in accordance with the embodiment of the present invention.
Figure 5:
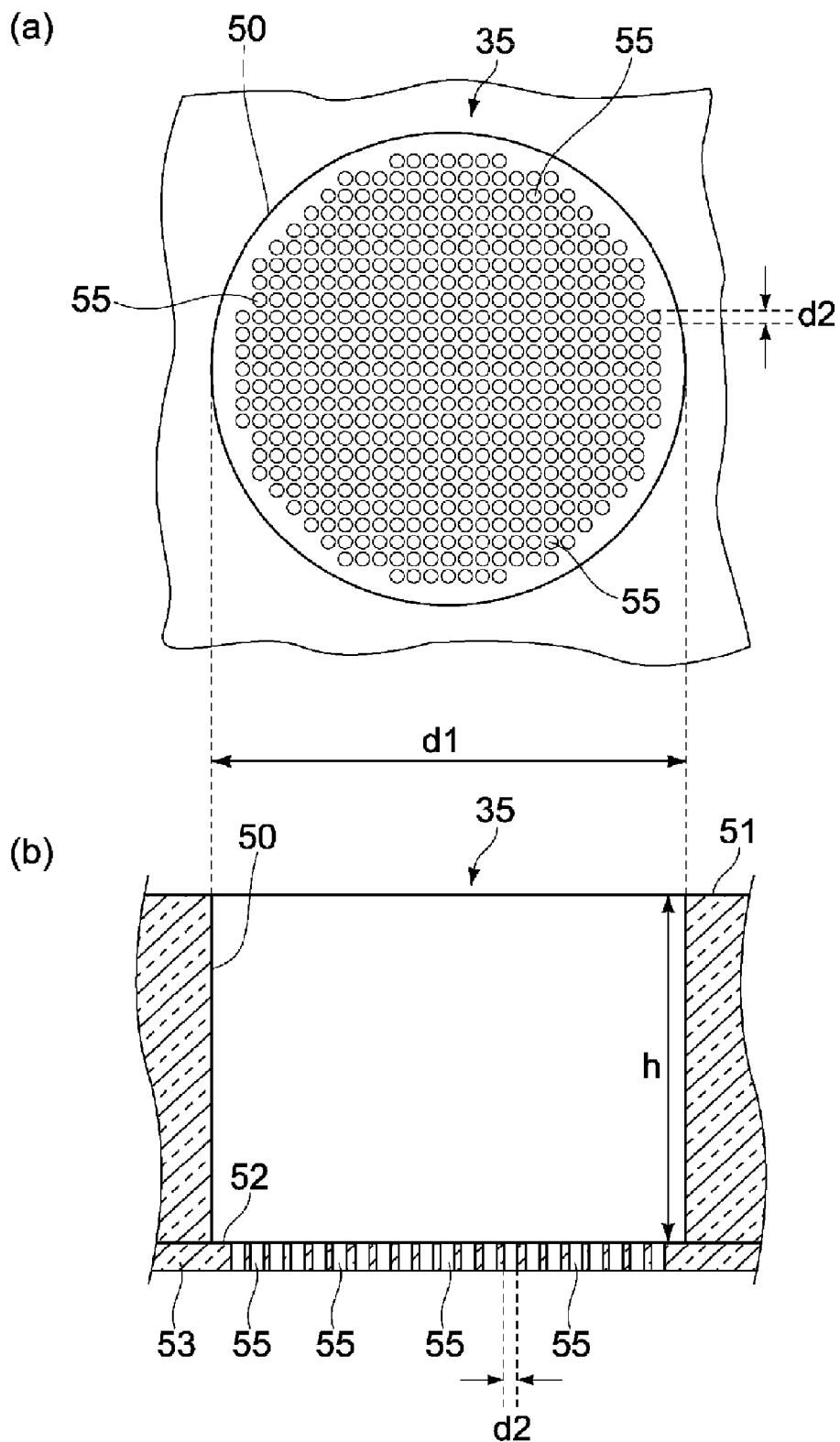
FIG. 5 offers enlarged views of one recess portion of a protein chip in accordance with the embodiment of the present invention.
Figure 6:
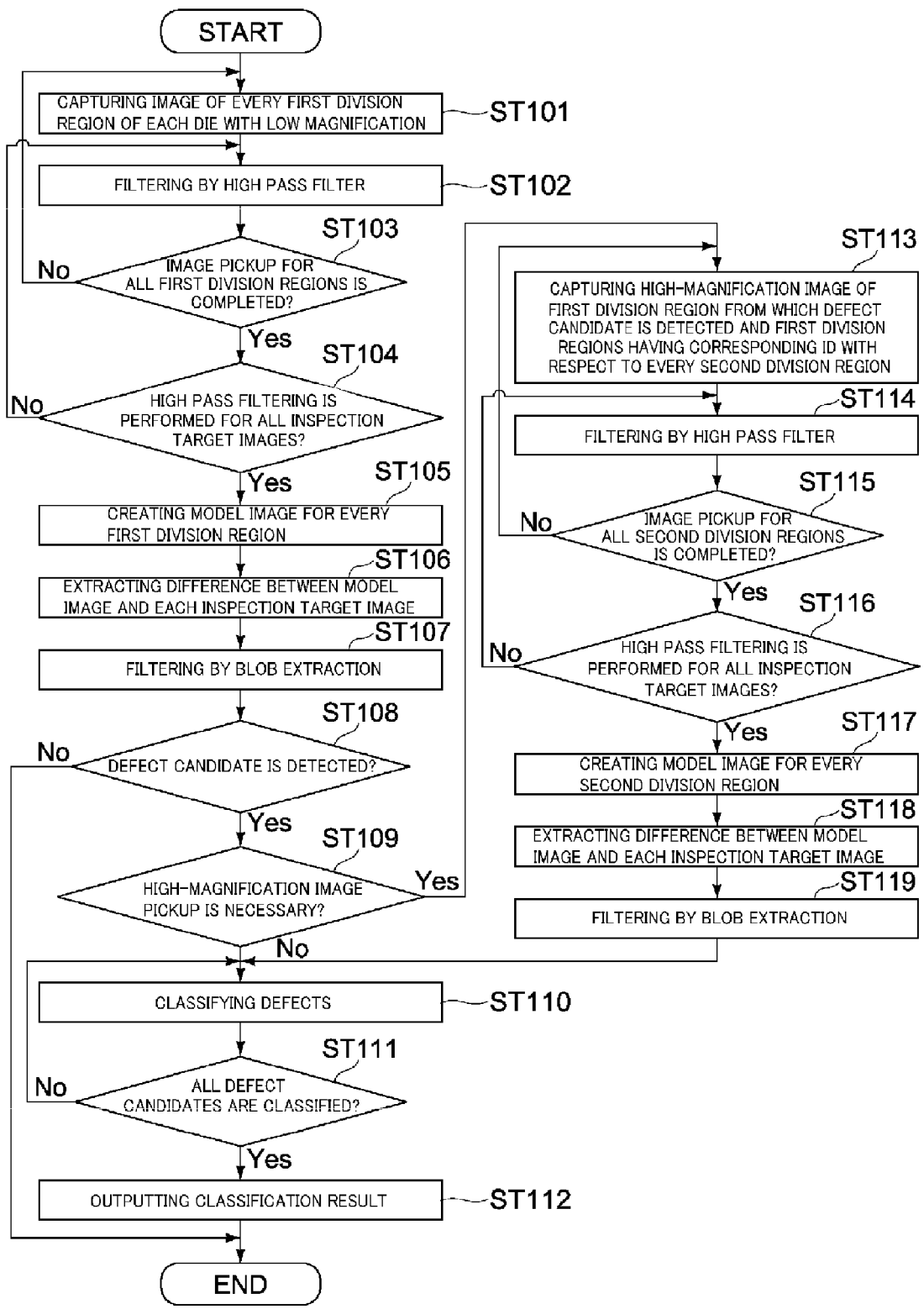
FIG. 6 provides a flowchart to schematically describe an operation sequence of the defect detecting apparatus until it detects a defect.
Figure 7:
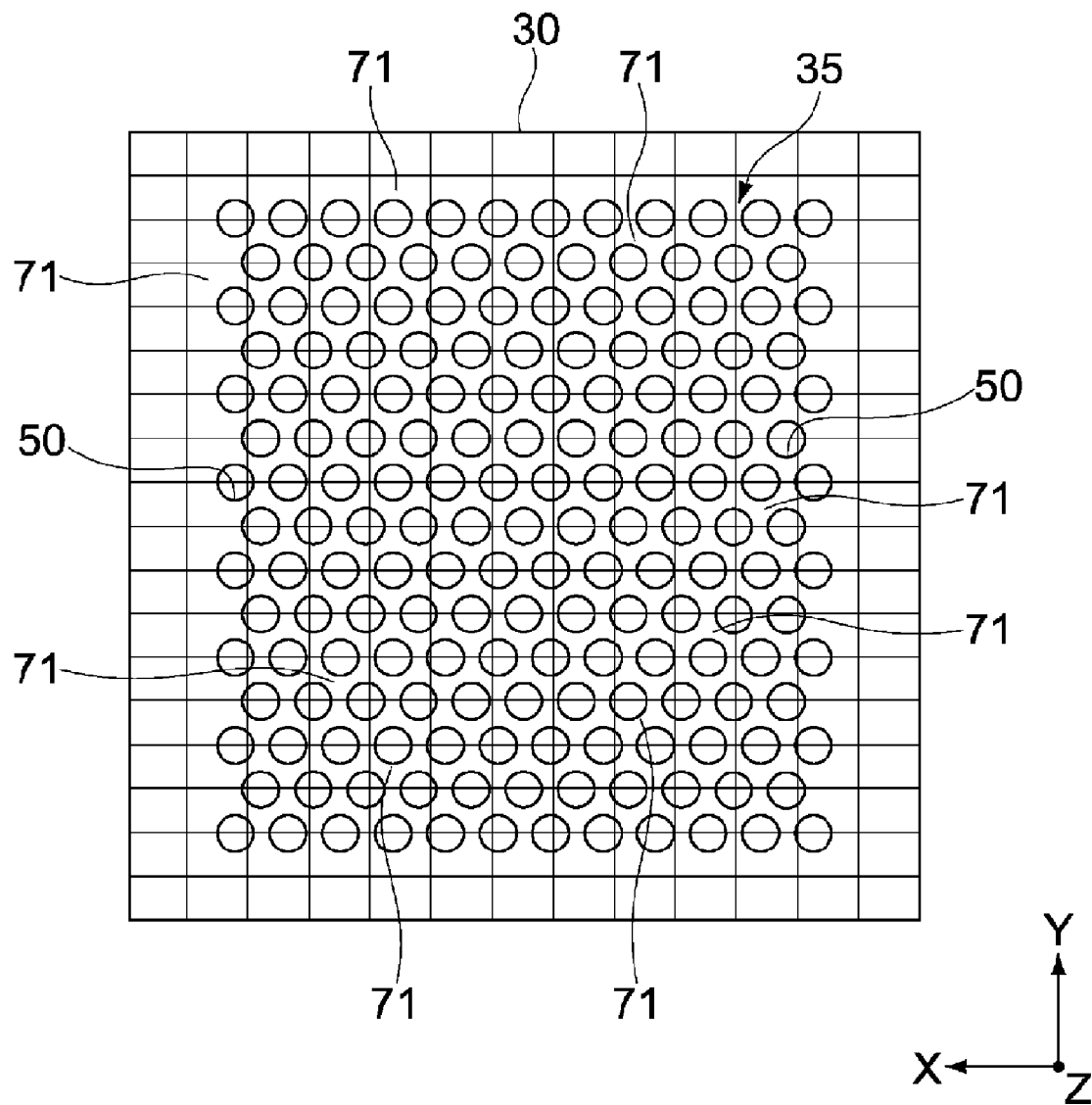
FIG. 7 sets forth a diagram illustrating a device obtained by dividing each die into a plurality of division regions in accordance with the embodiment of the present invention.
Figure 8:
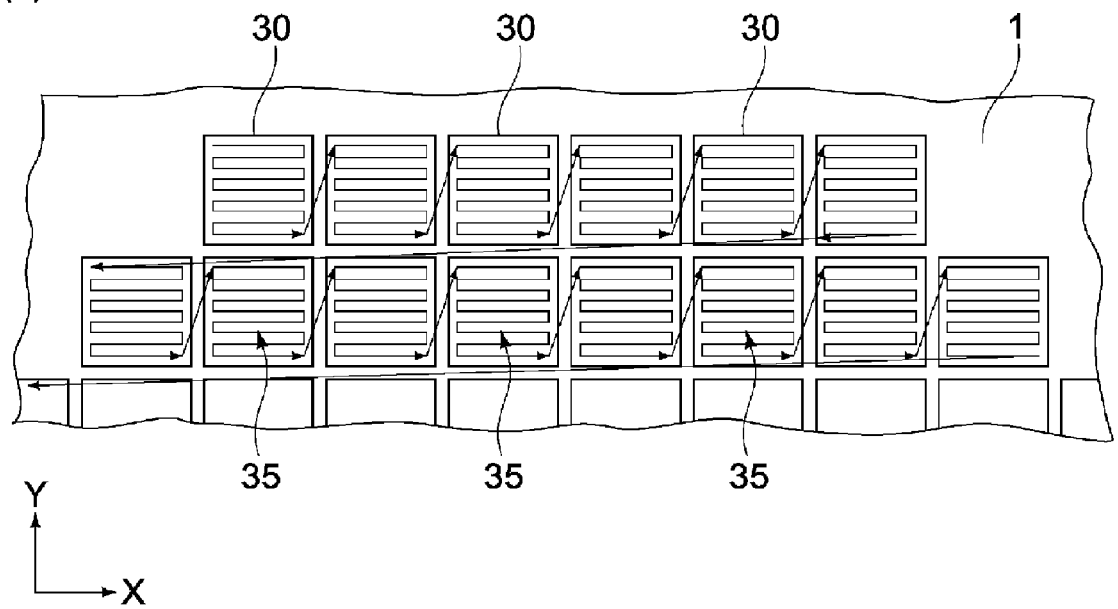
FIG. 8 depicts trajectories of image pickup positions when a CCD camera captures images of each division regions of the protein chip in accordance with the embodiment of the present invention.
Figure 8:
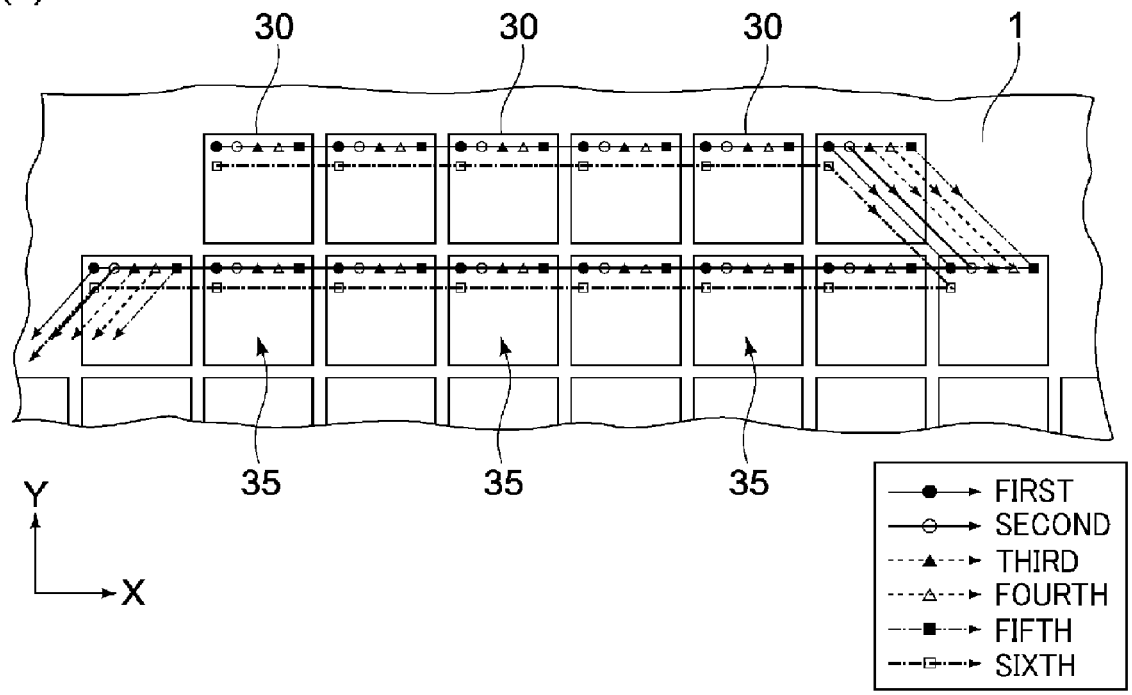
Figure 9:
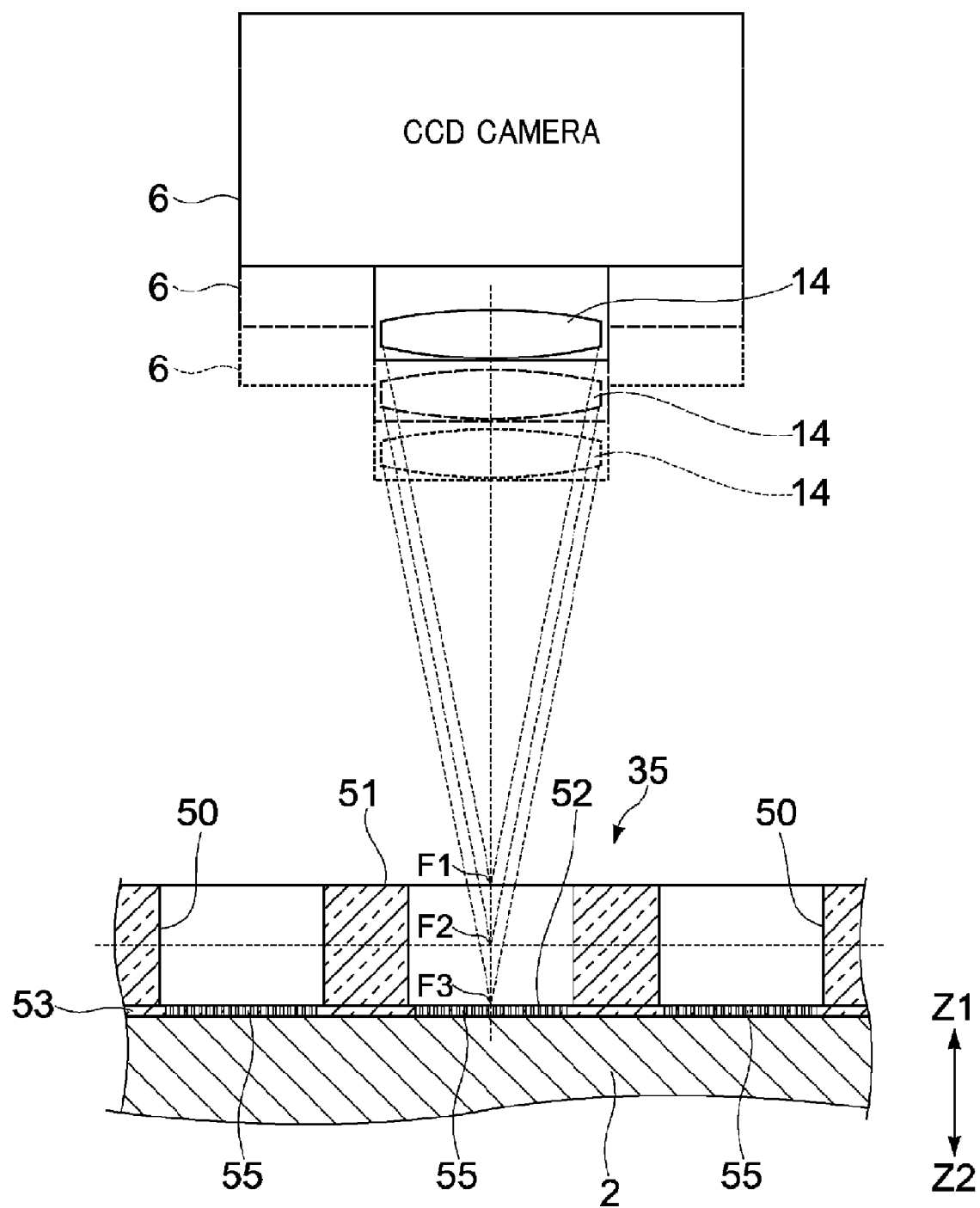
FIG. 9 illustrates a view of capturing inspection target images at different focal positions by the CCD camera in accordance with the embodiment of the present invention.
Figure 10:
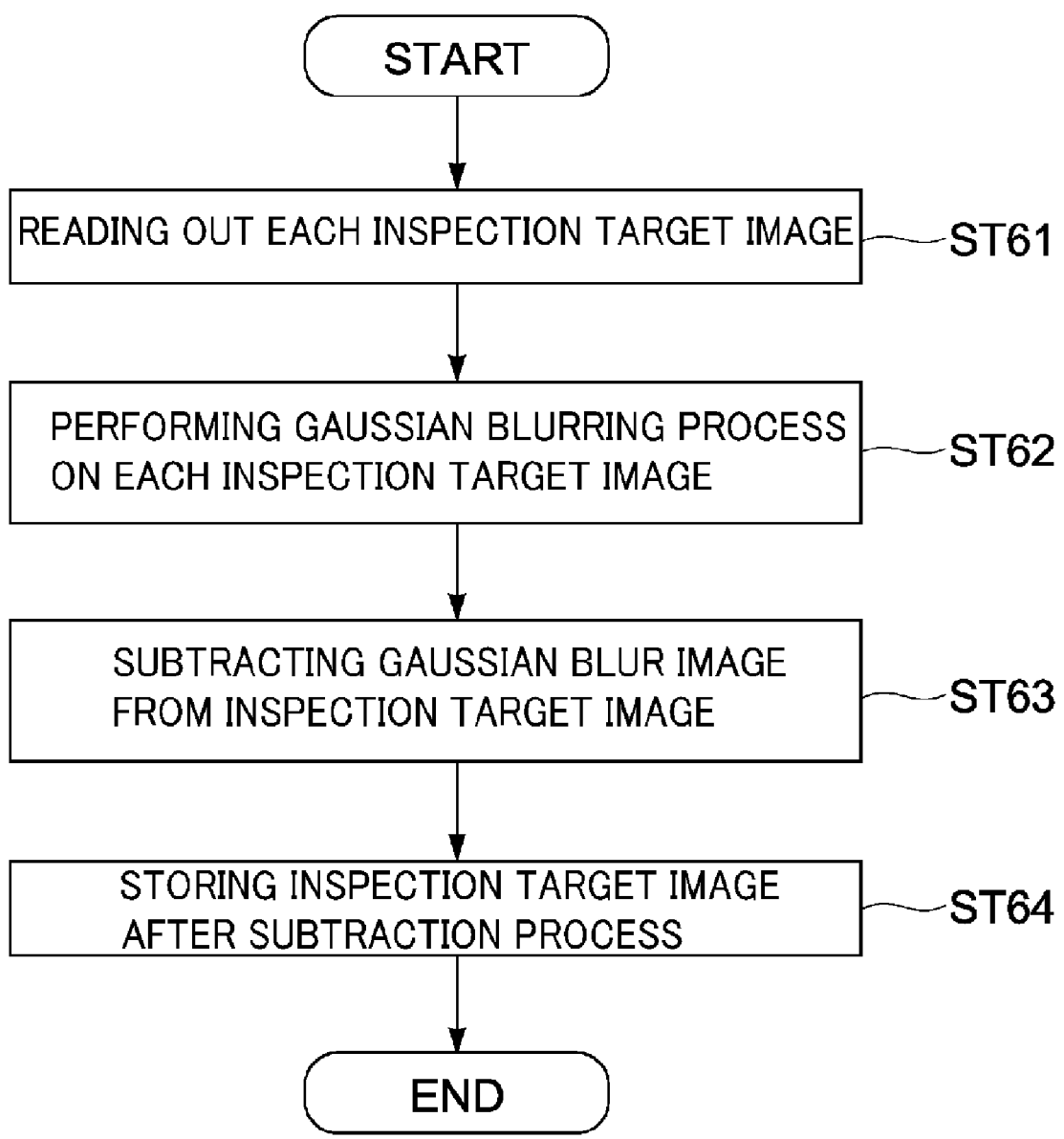
FIG. 10 presents a flowchart to describe a detailed sequence of a high pass filtering process in accordance with the embodiment of the present invention.
Figure 11:
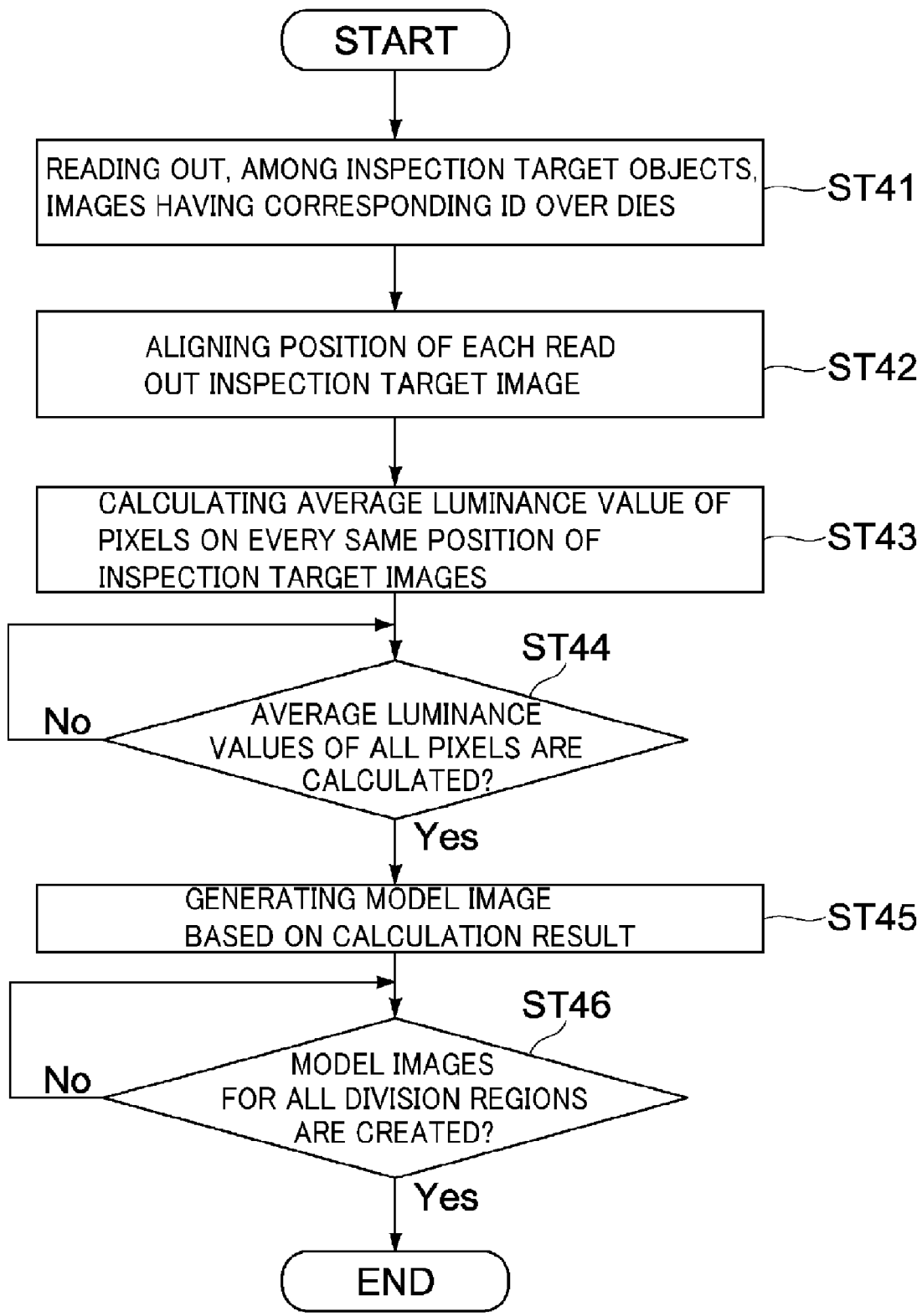
FIG. 11 depicts a flowchart to describe a process sequence until the image processing PC creates a model image in accordance with the embodiment of the present invention.
Figure 12:
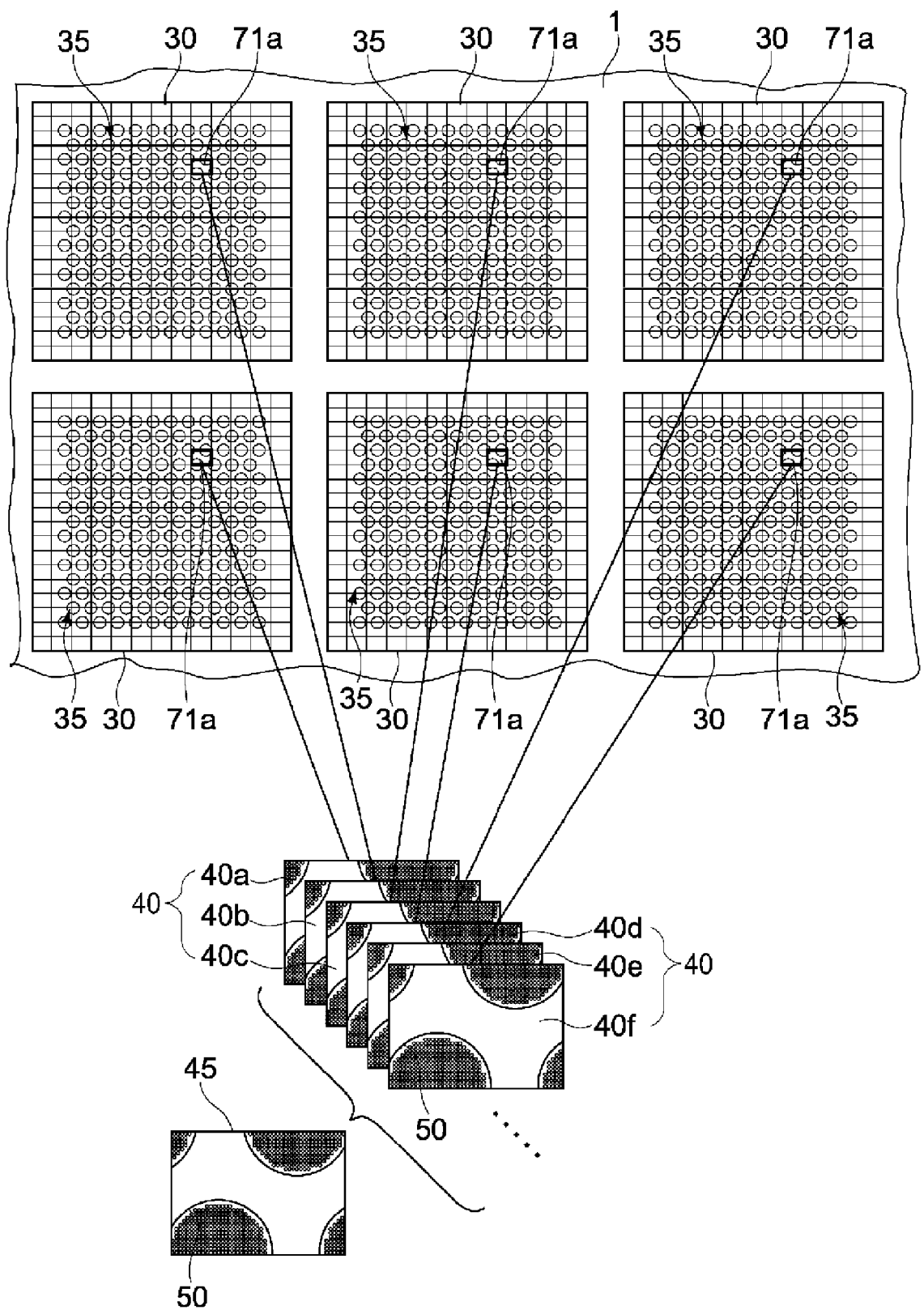
FIG. 12 schematically illustrates creation of the model image by the image processing PC in accordance with the embodiment of the present invention.
Figure 13:
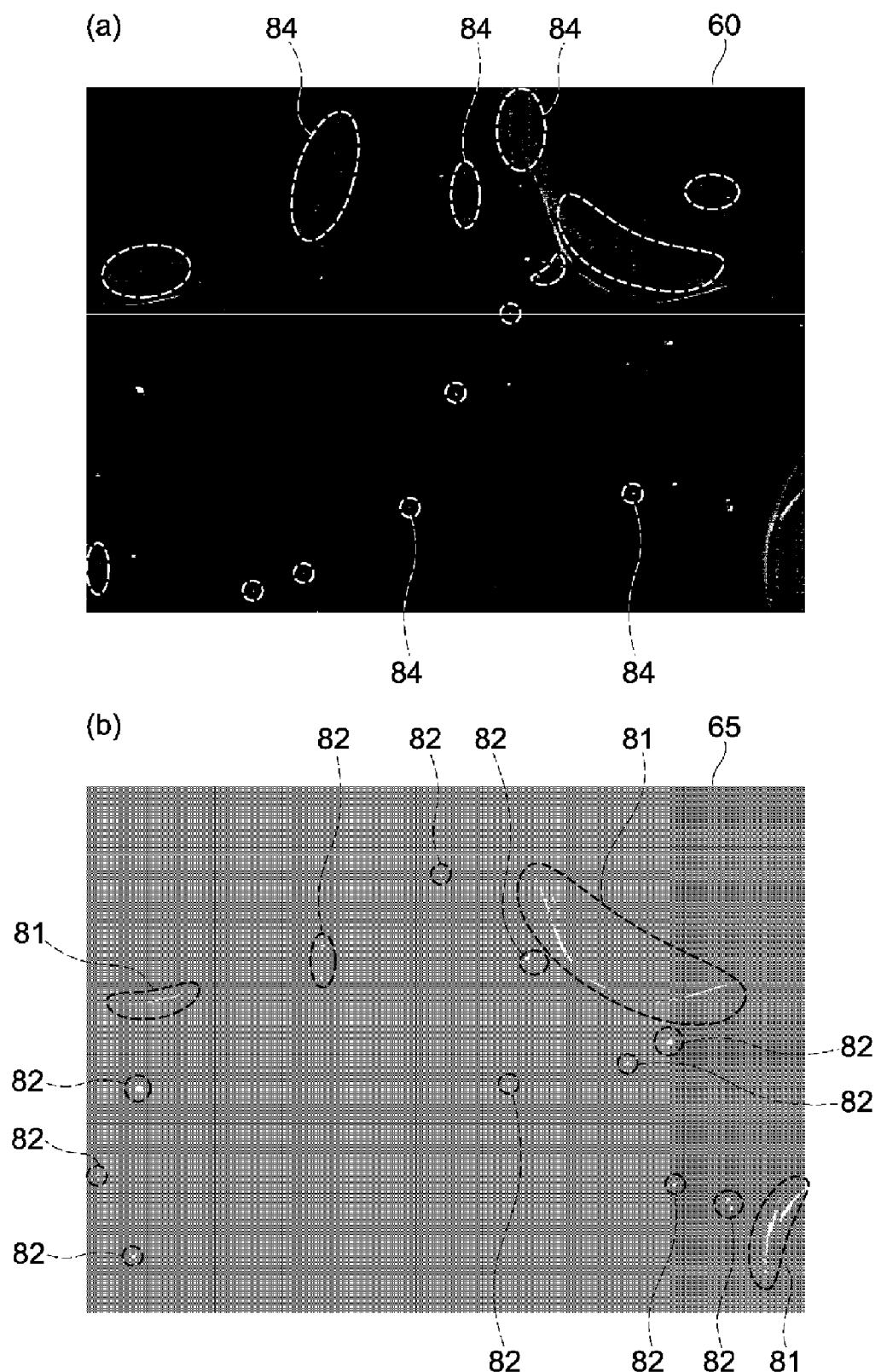
FIG. 13 illustrates difference images before and after a Blob extracting process in accordance with the embodiment of the present invention.
Figure 14:
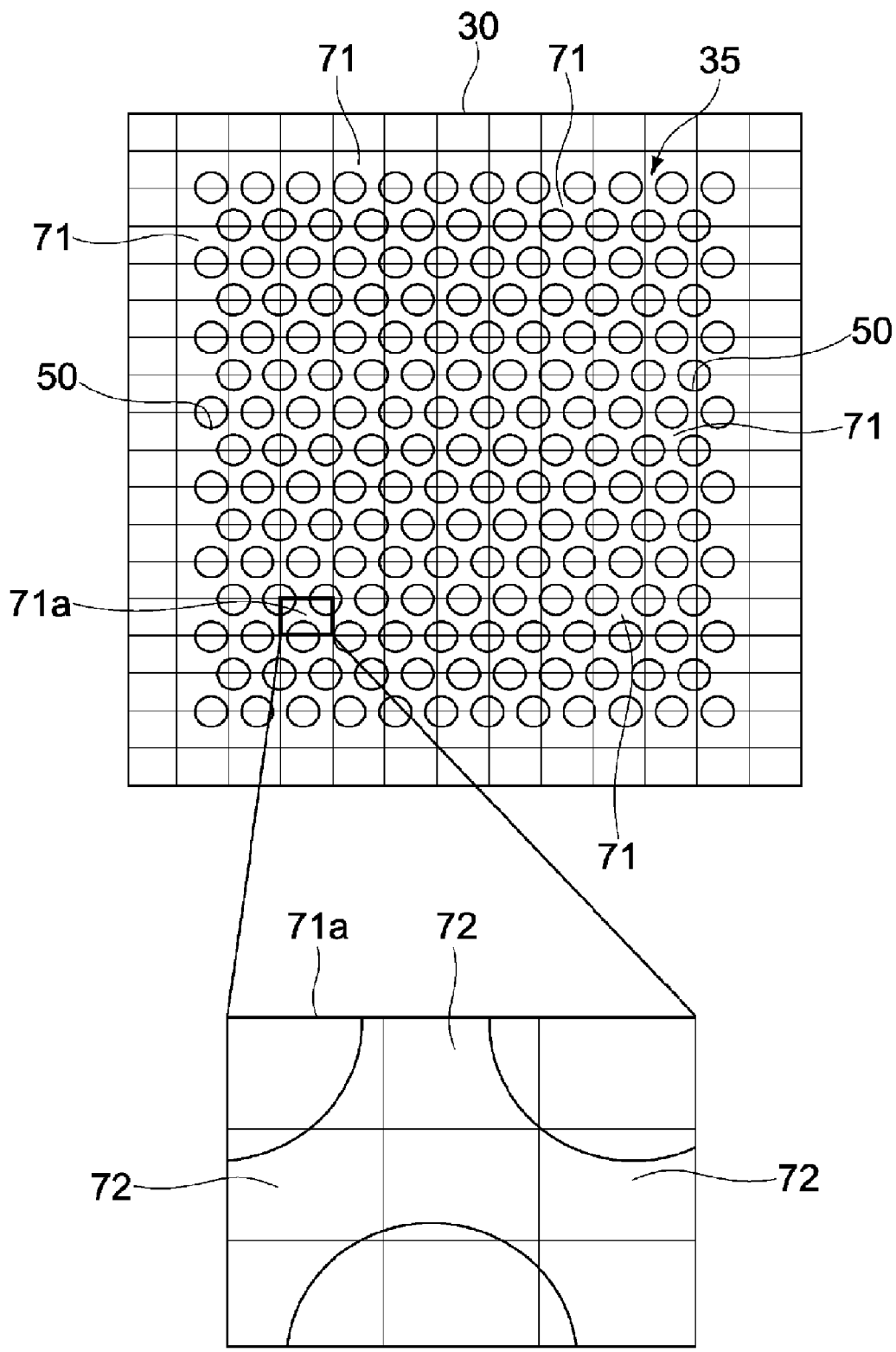
FIG. 14 schematically illustrates a high-magnification image pickup of each second division region with respect to a first division region from which a defect candidate is detected.
Figure 15:
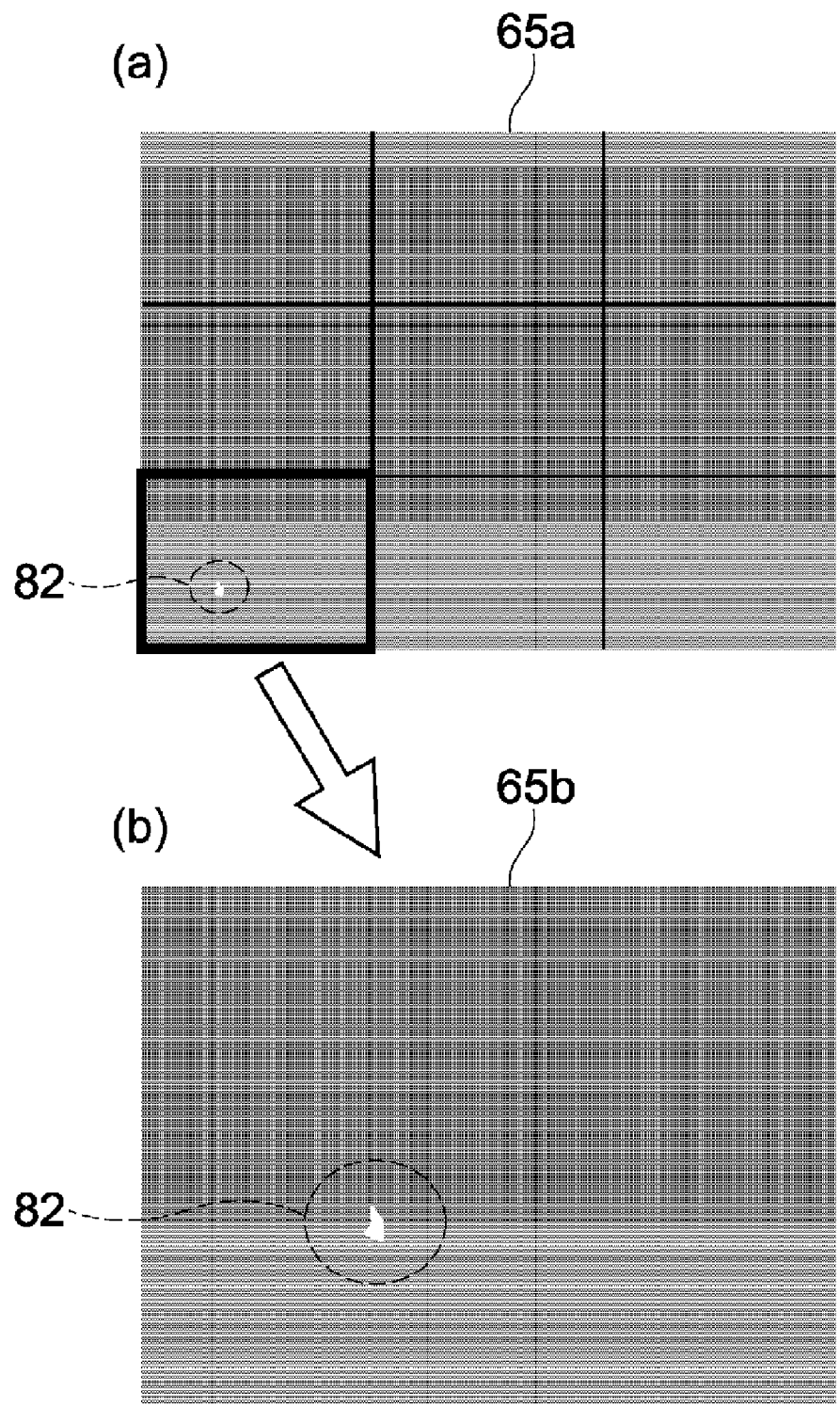
FIG. 15 provides Blob extraction images extracted from inspection target images of the first and second division regions in accordance with the embodiment of the present invention, respectively.
Figure 16:
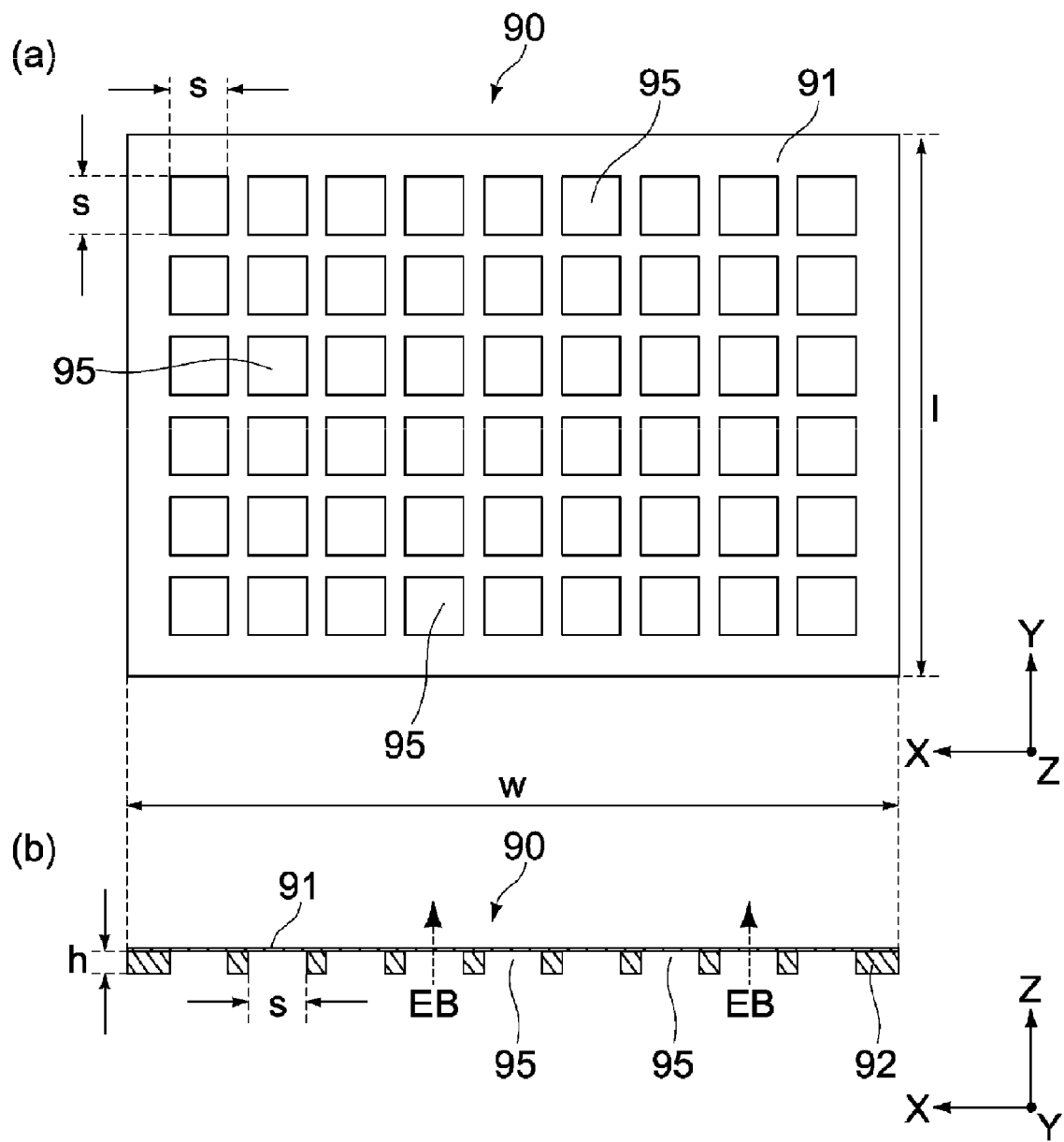
FIG. 16 provides exterior views of an electron beam irradiation plate in accordance with another embodiment of the present invention.

1: Semiconductor wafer (wafer)
3: XYZ stage
4: Motor
5: Encoder
6: CCD camera
7: Light source
10: Image processing PC
14: Lens
21: CPU
22: ROM
23: RAM
24: Input/output interface
25: HDD
26: Display unit
27: Manipulation input unit
30: Dies (semiconductor chips, chips)
35: Protein chip
40: Inspection target image
45: Model image
50: Recesses
51: Top surface
52: Bottom surface
53, 91: Thin film
55: Holes
60: Difference image
65: Blob extraction image
71: First division regions
72: Second division regions
81: Cracks
82: Foreign substances
84: Noises
90: Electron beam irradiation plate
92: Plate
95: Window holes
100: Defect detecting apparatus

What is claimed is:

1. A defect detecting apparatus comprising:
   an imaging unit that captures, with a first magnification, an image of a microstructure formed on each of a plurality of dies on a semiconductor wafer, with respect to every first division region obtained by dividing each die in plurality;
   a storage unit that stores therein the image of each first division region together with first identification information for identifying a position of each first division region within each die as a first inspection target image;
   a model image creating unit that creates an average image as a first model image for the every first identification information, the average image being obtained by averaging, among the first inspection target images, the first inspection target images of respective first division regions having the corresponding first identification information over the dies;
   a detecting unit that detects presence or absence of a defect of the microstructure on each first division region within one of the dies by comparing the first model image with each first inspection target image corresponding to the first identification information of the first model image;
   a control unit that controls the imaging unit such that the imaging unit captures, with a second magnification higher than the first magnification, an image of the microstructure on the first division region from which the defect is detected and microstructures on respective first division regions, within other dies, corresponding to the first identification information of the first division region from which the defect is detected, with respect to every second division region obtained by dividing each first division region in plurality; controls the storage unit to store therein the image of each second division region together with second identification information for identifying a position of each second division region within each die as a second inspection target image; and controls the model image creating unit to create an average image as a second model image for every second identification information, the second average image being obtained by averaging, among the second inspection target images, the second inspection target images of respective second division regions having the corresponding second identification information over the dies; and
   a defect classifying unit that determines the kind of the detected defect by comparing the second model image with each second inspection target image corresponding to the second identification information of the second model image.

2. The defect detecting apparatus of claim 1, wherein the storage unit stores therein feature point data indicating each feature point of plural kinds of defects,
   the detecting unit includes a first difference extracting unit that extracts a difference between the first model image and each first inspection target image as a first difference image, and
   the defect classifying unit includes a second difference extracting unit that extracts a difference between the second model image and each second inspection target image as a second difference image, a feature point extracting unit that extracts a feature point of a defect in the extracted difference images, and a classifying unit that determines the kind of the defect by comparing the extracted feature point with the feature point data.

3. The defect detecting apparatus of claim 2, wherein the storage unit includes a unit that updates the feature point data based on the feature point extracted by the feature point extracting unit.

4. The defect detecting apparatus of claim 2, wherein the control unit includes a unit that calculates the number of pixels that the defect in the first difference image detected by the first difference extracting unit occupies within the first difference image and performs an image pickup with the second magnification for every second division region if the number of pixels is smaller than a preset value, and
   the defect classifying unit determines the kind of the defect based on the first difference image if the image pickup with the second magnification is not performed.

5. The defect detecting apparatus of claim 1, wherein the model image creating unit includes a unit that calculates an average luminance value of every pixel constituting each inspection target image having the corresponding the identification information.

6. The defect detecting apparatus of claim 1, wherein the imaging unit successively captures the images of the microstructures on respective division regions having the corresponding identification information over the dies.

7. The defect detecting apparatus of claim 1, wherein after capturing the images of the microstructures in all the division regions on one die, the imaging unit captures the images of the microstructures in respective division regions on another die adjacent to said one die.

8. The defect detecting apparatus of claim 2, wherein the microstructures are screening test vessels including: a plurality of recesses each having a thin film shaped bottom surface and introducing therein a reagent and an antibody which cross-reacts with the reagent; and a plurality of holes provided in the bottom surface of each recess to discharge the reagent which does not react with the antibody.

9. The defect detecting apparatus of claim 8, wherein prior to averaging of the first inspection target images corresponding to the first identification information of the first model image and the second inspection target images corresponding to the second identification information of the second model image respectively, the model image creating unit aligns respective positions of the first and second inspection target images based on the shape of each recess of the vessel on the first and second inspection target images.

10. The defect detecting apparatus of claim 8, wherein prior to the extraction of the differences, the first and second difference extracting units align positions of the first model image and each first inspection target image, and align positions of the second model image and each second inspection target image, based on the shape of each recess of the vessel on the first and second model images and the shape of each recess on each first inspection target image corresponding to the first identification information of the first model image and each second inspection target image corresponding to having the second identification information of the second model image.

11. The defect detecting apparatus of claim 2, wherein the microstructure is an electron beam irradiation plate including a plate member having a plurality of window holes for irradiating electron beams and a thin film provided to cover each window hole.

12. The defect detecting apparatus of claim 11, wherein prior to averaging of the first inspection target images corresponding to the first identification information of the first model image and the second inspection target images corresponding to the second identification information of the second model image, the model image creating unit aligns respective positions of the first and second inspection target images based on the shape of each window hole of the electron beam irradiation plate on the first and second inspection target images.

13. The defect detecting apparatus of claim 11, wherein prior to the extraction of the differences, the first and second difference extracting units align positions of the first model image and each first inspection target image, and align positions of the second model image and each second inspection target image, based on the shape of each window hole of the electron beam irradiation plate on the first and second model images and the shape of each window hole on each first inspection target image corresponding to the first identification information of the first model image and each second inspection target image corresponding to the second identification information of the second model image.

14. A defect detecting method comprising:
capturing, with a first magnification, an image of a microstructure formed on each of a plurality of dies on a semiconductor wafer, with respect to every first division region obtained by dividing each die in plurality;
storing the image of each first division region together with a first identification information for identifying a position of each first division region within each die as a first inspection target image;
creating an average image as a first model image for the every first identification information, the average image being obtained by averaging, among the first inspection target images, the first inspection target images of respective first division regions having the corresponding first identification information over the dies;
detecting presence or absence of a defect of the microstructure on each first division region within one of the dies by comparing the first model image with each first inspection target image corresponding to the first identification information of the first model image;
capturing, with a second magnification higher than the first magnification, an image of the microstructure on the first division region from which the defect is detected and microstructures on respective first division regions, within other dies, corresponding to the first identification information of the first division region from which the defect is detected, with respect to every second division region obtained by dividing each first division region in plurality;
storing the image of each second division region together with second identification information for identifying a position of each second division region within each die as a second inspection target image;
creating an average image as a second model image for every second identification information, the second average image being obtained by averaging, among the second inspection target images, the second inspection target images of respective second division regions having the corresponding second identification information over the dies; and
determining the kind of the detected defect by comparing the second model image with each second inspection target image corresponding to the second identification information of the second model image.

15. An information processing apparatus comprising:
a storage unit that stores therein a captured image with a first magnification, of a microstructure formed on each of a plurality of dies on a semiconductor wafer, with respect to every first division region obtained by dividing each die in plurality together with first identification information for identifying a position of each first division region within each die as a first inspection target image;
a model image creating unit that creates an average image as a first model image, the average image being obtained by averaging, among the first inspection target images, the first inspection target images of respective first division regions having the corresponding first identification information over the dies;
a detecting unit that detects presence or absence of a defect of the microstructure on each first division region within one of the dies by comparing the first model image with each first inspection target image corresponding to the first identification information of the first model image;
a control unit that controls the storage unit to store therein captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image, and controls the model image creating unit to create an average image as second model image for every second identification information, the second average image being obtained by averaging, among the second inspection target images, the second inspection target images of respective second division regions having the corresponding second identification information over the dies; and a defect classifying unit that determines the kind of the detected defect by comparing the second model image with each second inspection target image corresponding to the second identification information of the second model image.

16. An information processing method comprising:

storing a captured image with a first magnification, of a microstructure formed on each of a plurality of dies on a semiconductor wafer, with respect to every first division region obtained by dividing each die in plurality together with first identification information for identifying a position of each first division region within each die as a first inspection target image;

creating an average image as a first model image, the average image being obtained by averaging, among the first inspection target images, the first inspection target images of respective first division regions having the corresponding first identification information over the dies;

detecting presence or absence of a defect of the microstructure on each first division region within one of the dies by comparing the first model image with each first inspection target image corresponding to the first identification information of the first model image;

storing captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image;

creating an average image as a second model image for every second identification information, the second average image being obtained by averaging, among the second inspection target images, the second inspection target images of respective second division regions having the corresponding second identification information over the dies; and determining the kind of the detected defect by comparing the second model image with each second inspection target image corresponding to the second identification information of the second model image.

17. A non-transitory computer-readable medium storing a program for executing, in an information processing apparatus, the processes of:

storing a captured image with a first magnification, of a microstructure formed on each of a plurality of dies on a semiconductor wafer, with respect to every first division region obtained by dividing each die in plurality together with first identification information for identifying a position of each first division region within each die as a first inspection target image;

creating an average image as a first model image, the average image being obtained by averaging, among the first inspection target images, the first inspection target images of respective first division regions having the corresponding first identification information over the dies;

detecting presence or absence of a defect of the microstructure on each first division region within one of the dies by comparing the first model image with each first inspection target image corresponding to the first identification information of the first model image;

storing captured images with a second magnification higher than the first magnification, of the microstructure on the first division region from which the defect is detected and microstructures on respective first division regions, within other dies, corresponding to the first identification information of the first division region from which the defect is detected, with respect to every second division region obtained by dividing each first division region in plurality together with second identification information for identifying a position of each second division region within each die as a second inspection target image;

creating an average image as a second model image for every second identification information, the second average image being obtained by averaging, among the second inspection target images, the second inspection target images of respective second division regions having the corresponding second identification information over the dies; and determining the kind of the detected defect by comparing the second model image with each second inspection target image corresponding to the second identification information of the second model image.

* * * * *

UNITED STATES PATENT AND TRADEMARK OFFICE
CERTIFICATE OF CORRECTION

| | | |
|---|---|---|
| PATENT NO. | : 7,783,102 B2 | |
| APPLICATION NO. | : 12/516605 | |
| DATED | : August 24, 2010 | |
| INVENTOR(S) | : Hiroshi Kawaragi | |

It is certified that error appears in the above-identified patent and that said Letters Patent is hereby corrected as shown below:

Column 10, line 2, insert the number -- 5 -- between "encoder" and "may"

Column 20, line 19, insert the number -- 40 -- between "image" and "of"

Signed and Sealed this
Twenty-eighth Day of December, 2010

David J. Kappos
*Director of the United States Patent and Trademark Office*